US012773091B2

(12) United States Patent
Ouyang et al.

(10) Patent No.: US 12,773,091 B2
(45) Date of Patent: Oct. 27, 2026

(54) HAND-HELD, ROBOTIC-ASSISTED ENDOSCOPE WITH POSITION TRACKING

(71) Applicant: MicronVision Corp., Bellevue, WA (US)

(72) Inventors: Xiaolong Ouyang, Bellevue, WA (US); James Ouyang, Bellevue, WA (US); Diana Ouyang, Bellevue, WA (US); Shih-Ping Wang, Los Altos, CA (US)

(73) Assignee: MicronVision Corp., Bellevue, WA (US)

( * ) Notice: Subject to any disclaimer, the term of this patent is extended or adjusted under 35 U.S.C. 154(b) by 901 days.

(21) Appl. No.: 17/941,884

(22) Filed: Sep. 9, 2022

(65) Prior Publication Data

US 2023/0117151 A1 Apr. 20, 2023

Related U.S. Application Data

(60) Provisional application No. 63/332,233, filed on Apr. 18, 2022, provisional application No. 63/283,367, (Continued)

(51) Int. Cl.

| | |
|---|---|
| ***A61B 1/00*** | (2006.01) |
| ***A61B 34/30*** | (2016.01) |
| ***A61B 90/00*** | (2016.01) |

(52) U.S. Cl.
CPC ...... *A61B 1/00006* (2013.01); *A61B 1/00009* (2013.01); *A61B 1/00096* (2013.01); (Continued)

(58) Field of Classification Search
CPC ............ A61B 1/00006; A61B 1/00009; A61B 1/00096; A61B 34/30; A61B 90/361; A61B 2034/301; A61B 2090/365
See application file for complete search history.

(56) References Cited

U.S. PATENT DOCUMENTS 4,854,302 A 8/1989 Allred, III
4,979,497 A 12/1990 Matsura
(Continued)

FOREIGN PATENT DOCUMENTS

CN 102858275 1/2013
EP 1690512 8/2006
(Continued)

OTHER PUBLICATIONS

International Search Report and Written Opinion of PCT/US2016/18670, dated Jul. 12, 2016.
(Continued)

*Primary Examiner* — Michael J Carey
*Assistant Examiner* — William B Chou
(74) *Attorney, Agent, or Firm* — Wissing Miller LLP

(57) ABSTRACT

A compact, hand-held, robotic assisted endoscopic system configured to derive the position and/or orientation CamPose of a distal part of a single-use portion relative to coordinates HandPose of a reusable portion of an endoscope and display juxtaposed images of an object such a patient's organ being diagnosed or treated in a medical procedure with the endoscope and the distal part of the endoscope, and to provide guidance to the system user with display of images such as prior images of the object, standardized images of the object of tutorial images related to the medical procedure.

9 Claims, 24 Drawing Sheets

Related U.S. Application Data filed on Nov. 26, 2021, provisional application No. 63/282,108, filed on Nov. 22, 2021, provisional application No. 63/256,634, filed on Oct. 18, 2021.

(52) U.S. Cl.
CPC ............ *A61B 34/30* (2016.02); *A61B 90/361* (2016.02); *A61B 2034/301* (2016.02); *A61B 2090/365* (2016.02)

(56) References Cited

U.S. PATENT DOCUMENTS

| | | | |
|---|---|---|---|
| 5,010,876 | A | 4/1991 | Henley |
| 5,188,093 | A | 2/1993 | Lafferty |
| 5,281,214 | A | 1/1994 | Wilkins |
| 5,323,767 | A | 6/1994 | Lafferty |
| 5,329,936 | A | 7/1994 | Lafferty |
| 5,390,117 | A | 2/1995 | Graf et al. |
| 5,486,155 | A | 1/1996 | Muller |
| 5,549,547 | A | 8/1996 | Cohen |
| 5,569,163 | A | 10/1996 | Francis |
| 5,666,561 | A | 9/1997 | Stephenson |
| 5,667,472 | A | 9/1997 | Finn |
| 5,667,476 | A | 9/1997 | Frassica et al. |
| 5,785,644 | A | 7/1998 | Grabover |
| 5,860,953 | A | 1/1999 | Snoke |
| 5,873,814 | A | 2/1999 | Adair |
| 5,928,137 | A | 7/1999 | Green |
| 5,935,141 | A | 8/1999 | Weldon |
| 5,957,947 | A | 9/1999 | Wattiez |
| 6,007,531 | A | 12/1999 | Snoke |
| 6,007,546 | A | 12/1999 | Snow |
| 6,017,322 | A | 1/2000 | Snoke |
| 6,033,378 | A | 3/2000 | Lundquist |
| 6,059,719 | A | 5/2000 | Yamamato et al. |
| 6,095,970 | A | 8/2000 | Hidaka |
| 6,174,307 | B1 | 1/2001 | Daniel |
| 6,210,416 | B1 | 4/2001 | Chu |
| 6,211,904 | B1 | 4/2001 | Adair |
| 6,221,007 | B1 | 4/2001 | Green |
| 6,221,070 | B1 | 4/2001 | Tu et al. |
| 6,261,226 | B1 | 7/2001 | McKenna |
| 6,280,386 | B1 | 8/2001 | Alfano |
| 6,331,174 | B1 | 12/2001 | Reinhard |
| 6,387,043 | B1 | 5/2002 | Yoon |
| 6,398,743 | B1 | 6/2002 | Halseth |
| 6,507,699 | B2 | 1/2003 | Lemoine |
| 6,518,823 | B1 | 2/2003 | Kawai |
| 6,793,882 | B1 | 9/2004 | Verschuur |
| 6,917,380 | B1 | 7/2005 | Tay |
| 7,256,446 | B2 | 8/2007 | Hu |
| 7,428,378 | B1 | 9/2008 | Warpakowski |
| 7,507,205 | B2 | 3/2009 | Borovsky |
| 7,591,799 | B2 | 9/2009 | Selkee |
| 7,606,609 | B2 | 10/2009 | Muranushi |
| 7,780,650 | B2 | 8/2010 | Frassica |
| 7,798,995 | B2 | 9/2010 | Yue |
| 7,931,616 | B2 | 4/2011 | Selkee |
| 7,946,981 | B1 | 5/2011 | Cubb |
| 8,052,609 | B2 | 11/2011 | Harhen |
| 8,057,464 | B2 | 11/2011 | Chen |
| 8,187,171 | B2 | 5/2012 | Irion |
| 8,197,398 | B2 | 6/2012 | Scholly |
| 8,235,975 | B2 | 8/2012 | Chen |
| 8,361,775 | B2 | 1/2013 | Flower |
| 8,460,182 | B2 | 6/2013 | Ouyang |
| 8,523,808 | B2 | 9/2013 | Selkee |
| 8,696,552 | B2 | 4/2014 | Whitman |
| 8,803,960 | B2 | 8/2014 | Sonnenschein |
| 8,834,357 | B2 | 9/2014 | Oskin |
| 8,845,522 | B2 | 9/2014 | McIntyre |
| 8,952,312 | B2 | 2/2015 | Blanqart |
| 8,998,844 | B2 | 4/2015 | Reed |
| 9,649,014 | B2 | 5/2017 | Ouyang |
| 9,736,342 | B2 | 8/2017 | Mueckl |
| 9,895,048 | B2 | 2/2018 | Ouyang |
| 10,278,563 | B2 | 5/2019 | Ouyang |
| 10,292,571 | B2 | 5/2019 | Ouyang |
| 10,595,710 | B2 | 3/2020 | Gill |
| 11,330,973 | B2 | 5/2022 | Ouyang |
| 2001/0007051 | A1 | 7/2001 | Nakashima |
| 2001/0049509 | A1 | 12/2001 | Sekine |
| 2003/0016284 | A1 | 1/2003 | Squilla |
| 2003/0023142 | A1 | 1/2003 | Grabover |
| 2003/0078476 | A1 | 4/2003 | Hill |
| 2003/0078502 | A1 | 4/2003 | Miyaki et al. |
| 2003/0151680 | A1 | 8/2003 | McDermott |
| 2003/0199735 | A1 | 10/2003 | Dickopp |
| 2004/0054254 | A1 | 3/2004 | Miyake |
| 2004/0054259 | A1 | 3/2004 | Hasegawa |
| 2004/0138558 | A1 | 7/2004 | Dunki-Jacobs |
| 2004/0162572 | A1 | 8/2004 | Sauer |
| 2005/0010178 | A1 | 1/2005 | Katz |
| 2005/0049459 | A1 | 3/2005 | Hern |
| 2005/0085695 | A1 | 4/2005 | Sherner |
| 2005/0154262 | A1 | 7/2005 | Banik |
| 2005/0159646 | A1 | 7/2005 | Nordstrom |
| 2005/0177027 | A1 | 8/2005 | Hirata |
| 2005/0264687 | A1 | 12/2005 | Murayama |
| 2005/0277874 | A1 | 12/2005 | Selkee |
| 2005/0277875 | A1 | 12/2005 | Selkee |
| 2006/0052710 | A1 | 3/2006 | Miura |
| 2006/0063976 | A1 | 3/2006 | Aizenfeld |
| 2006/0114986 | A1 | 6/2006 | Knapp |
| 2006/0152601 | A1 | 7/2006 | Parekh |
| 2006/0167340 | A1 | 7/2006 | Peas |
| 2006/0171693 | A1 | 8/2006 | Todd |
| 2006/0173245 | A1 | 8/2006 | Todd |
| 2006/0259124 | A1 | 11/2006 | Matsuoka |
| 2006/0287576 | A1 | 12/2006 | Tsuji |
| 2007/0060789 | A1 | 3/2007 | Uchimura |
| 2007/0081920 | A1 | 4/2007 | Murphy |
| 2007/0117437 | A1 | 5/2007 | Boehnlein |
| 2007/0129604 | A1 | 6/2007 | Hatcher |
| 2007/0162095 | A1 | 7/2007 | Kimmel |
| 2007/0167678 | A1 | 7/2007 | Moskowitz |
| 2007/0167868 | A1 | 7/2007 | Sauer |
| 2007/0173693 | A1 | 7/2007 | Refael |
| 2007/0188604 | A1 | 8/2007 | Miyamoto |
| 2007/0197875 | A1 | 8/2007 | Osaka |
| 2007/0210162 | A1 | 9/2007 | Keen |
| 2007/0225556 | A1 | 9/2007 | Ortiz |
| 2007/0238927 | A1 | 10/2007 | Ueno |
| 2008/0004642 | A1 | 1/2008 | Birk |
| 2008/0071144 | A1 | 3/2008 | Kimmel |
| 2008/0097550 | A1 | 4/2008 | Dicks |
| 2008/0108869 | A1 | 5/2008 | Sanders |
| 2008/0195125 | A1 | 8/2008 | Orbay |
| 2008/0195128 | A1 | 8/2008 | Orbay |
| 2008/0225410 | A1 | 9/2008 | Ning |
| 2008/0234547 | A1 | 9/2008 | Irion et al. |
| 2008/0255416 | A1 | 10/2008 | Gilboa |
| 2008/0262306 | A1 | 10/2008 | Kawai |
| 2008/0300456 | A1 | 12/2008 | Irion |
| 2009/0027489 | A1 | 1/2009 | Takemura |
| 2009/0065565 | A1 | 3/2009 | Lemoine |
| 2009/0076321 | A1 | 3/2009 | Suyama |
| 2009/0076328 | A1 | 3/2009 | Root |
| 2009/0080214 | A1 | 3/2009 | Watanabe |
| 2009/0105538 | A1 | 4/2009 | Van Dam |
| 2009/0118580 | A1 | 5/2009 | Sun |
| 2009/0118641 | A1 | 5/2009 | Van Dam |
| 2009/0149713 | A1 | 6/2009 | Niida |
| 2009/0225159 | A1 | 9/2009 | Schneider |
| 2009/0227897 | A1 | 9/2009 | Wendt |
| 2009/0286412 | A1 | 11/2009 | Ikeda |
| 2009/0287663 | A1 | 11/2009 | Takeuchi |
| 2010/0026201 | A1 | 2/2010 | Byun et al. |
| 2010/0069834 | A1 | 3/2010 | Schultz |
| 2010/0094216 | A1 | 4/2010 | Yue |
| 2010/0095969 | A1 | 4/2010 | Schwartz |
| 2010/0101569 | A1 | 4/2010 | Kim |
| 2010/0121142 | A1 | 5/2010 | Ouyang |
| 2010/0157039 | A1 | 6/2010 | Sugai |

(56) References Cited

U.S. PATENT DOCUMENTS

| | | | |
|---|---|---|---|
| 2010/0160914 A1 | 6/2010 | Bastian | |
| 2010/0168827 A1 | 7/2010 | Schultz | |
| 2010/0191051 A1 | 7/2010 | Miyake | |
| 2010/0191053 A1 | 7/2010 | Garcia | |
| 2010/0234736 A1 | 9/2010 | Cor | |
| 2011/0009694 A1 | 1/2011 | Schultz | |
| 2011/0034769 A1 | 2/2011 | Adair | |
| 2011/0037876 A1 | 2/2011 | Talbert | |
| 2011/0054446 A1 | 3/2011 | Schultz | |
| 2011/0092775 A1 | 4/2011 | Deshmukh | |
| 2011/0105839 A1 | 5/2011 | Hoffman | |
| 2011/0112622 A1 | 5/2011 | Phan | |
| 2011/0130627 A1 | 6/2011 | McGrail | |
| 2011/0211115 A1 | 9/2011 | Tsai | |
| 2011/0213206 A1 | 9/2011 | Boutillette | |
| 2011/0245602 A1 | 10/2011 | Brannon | |
| 2011/0288482 A1 | 11/2011 | Farrell | |
| 2012/0016191 A1 | 1/2012 | Ito | |
| 2012/0040305 A1 | 2/2012 | Karazivan | |
| 2012/0053515 A1 | 3/2012 | Crank | |
| 2012/0100729 A1 | 4/2012 | Edidin | |
| 2012/0165916 A1 | 6/2012 | Jordan | |
| 2012/0178991 A1 | 7/2012 | Clark | |
| 2012/0226103 A1 | 9/2012 | Gunday | |
| 2012/0236138 A1 | 9/2012 | Liu | |
| 2012/0245242 A1 | 9/2012 | Peiffer | |
| 2012/0245418 A1 | 9/2012 | Boulais | |
| 2012/0253116 A1 | 10/2012 | Sniffin | |
| 2012/0259203 A1 | 10/2012 | Devereux | |
| 2012/0286020 A1 | 11/2012 | Smith | |
| 2012/0289858 A1 | 11/2012 | Ouyang | |
| 2013/0035553 A1 | 2/2013 | Kongstorum | |
| 2013/0046142 A1 | 2/2013 | Remijan | |
| 2013/0057667 A1 | 3/2013 | McGrath | |
| 2013/0150672 A1 | 6/2013 | Fujitani | |
| 2013/0172676 A1 | 7/2013 | Levy | |
| 2013/0225921 A1 | 8/2013 | Liu | |
| 2013/0253402 A1 | 9/2013 | Badawi | |
| 2013/0289559 A1 | 10/2013 | Reid | |
| 2013/0324973 A1 | 12/2013 | Reed | |
| 2013/0345514 A1 | 12/2013 | Manion | |
| 2014/0022649 A1 | 1/2014 | Echhardt | |
| 2014/0107416 A1 | 4/2014 | Bimkrant | |
| 2014/0111634 A1 | 4/2014 | Mueckl | |
| 2014/0154399 A1 | 6/2014 | Weikart | |
| 2014/0180007 A1 | 6/2014 | Edidin | |
| 2014/0213848 A1 | 7/2014 | Moskowitz | |
| 2014/0228635 A1 | 8/2014 | Tuliakov | |
| 2014/0275763 A1 | 9/2014 | King | |
| 2014/0296866 A1 | 10/2014 | Salman | |
| 2014/0323991 A1 | 10/2014 | Tang | |
| 2015/0005575 A1 | 1/2015 | Kobayashi | |
| 2015/0011830 A1 | 1/2015 | Hunter | |
| 2015/0018622 A1 | 1/2015 | Tesar | |
| 2015/0018710 A1 | 1/2015 | Furlong | |
| 2015/0150441 A1 | 6/2015 | Ouyang | |
| 2015/0164313 A1 | 6/2015 | Oyuang | |
| 2015/0196197 A1 | 7/2015 | Kienzle | |
| 2015/0238251 A1 | 8/2015 | Shikhman | |
| 2015/0297311 A1 | 10/2015 | Tesar | |
| 2016/0073853 A1 | 3/2016 | Venkatesan et al. | |
| 2016/0077008 A1 | 3/2016 | Takasu | |
| 2016/0174819 A1 | 6/2016 | Ouyang | |
| 2016/0334694 A1 | 11/2016 | Liu | |
| 2016/0367119 A1 | 12/2016 | Ouyang | |
| 2017/0086651 A1 | 3/2017 | Sato | |
| 2017/0188793 A1 | 7/2017 | Ouyang | |
| 2017/0188795 A1 | 7/2017 | Ouyang | |
| 2017/0215699 A1 | 8/2017 | Ouyang | |
| 2017/0295347 A1 | 10/2017 | Schneider | |
| 2017/0310858 A1 | 10/2017 | Mueckl | |
| 2018/0132700 A1 | 5/2018 | Ouyang | |
| 2018/0184892 A1 | 7/2018 | Truckai | |
| 2018/0235441 A1 | 8/2018 | Huang | |
| 2018/0256009 A1 | 9/2018 | Ouyang | |
| 2019/0029497 A1 | 1/2019 | Mirza | |
| 2019/0142262 A1 | 5/2019 | Inglis | |
| 2019/0216325 A1 | 7/2019 | Ouyang | |
| 2019/0223691 A1 | 7/2019 | Takatsuji | |
| 2019/0246873 A1 | 8/2019 | Lu | |
| 2019/0246884 A1 | 8/2019 | Lu et al. | |
| 2019/0282073 A1 | 9/2019 | Truckai | |
| 2019/0320879 A1 | 10/2019 | Langell | |
| 2019/0374095 A1 | 12/2019 | Lord | |
| 2020/0204776 A1 | 6/2020 | Themelis | |
| 2020/0214739 A1 | 7/2020 | Shi | |
| 2020/0275827 A1 | 9/2020 | Weise | |
| 2021/0121245 A1* | 4/2021 | Hufford | A61B 90/361 |
| 2021/0228806 A1 | 7/2021 | Streeter | |
| 2021/0386503 A1* | 12/2021 | Healy | G16H 50/20 |
| 2021/0401277 A1 | 12/2021 | Ouyang | |

FOREIGN PATENT DOCUMENTS

| | | |
|---|---|---|
| EP | 2560589 | 4/2010 |
| EP | 3384879 | 4/2011 |
| EP | 2749258 | 7/2014 |
| EP | 3078354 | 10/2016 |
| JP | 2009148420 | 7/2009 |
| WO | 2011133792 | 10/2011 |
| WO | 2012060932 | 5/2012 |
| WO | 2014031192 | 2/2014 |
| WO | 2014065901 | 5/2015 |
| WO | 2016032729 | 3/2016 |
| WO | 2016040131 | 3/2016 |
| WO | 2016137838 | 9/2016 |
| WO | 2018136950 | 7/2018 |
| WO | 2019237003 | 12/2019 |

OTHER PUBLICATIONS

International Search Report and Written Opinion of PCT/US2018/014880, dated Jun. 6, 2018.

International Search Report and Written Opinion of PCT/US2018/065396, dated Feb. 24, 2017.

International Search Report and Written Opinion of PCT/US2021/050095 dated Dec. 17, 2021.

International Search Report and Written Opinion of PCT/US2019/036060 dated Aug. 27, 2019.

International Search Report and Written Opinion of PCT/US2017/053171 mailed Dec. 5, 2017.

International Preliminary Report on Patentability of PCT/US2017/053171 completed on Jul. 1, 2019.

Chinese Office Action for Application No. 202221943644.0, dated Dec. 21, 2022.

Extended European Search Report for EP19816177, dated Feb. 15, 2022.

International Preliminary Report on Patentability for PCT/US2021/050095, dated Mar. 23, 2023.

* cited by examiner

AI and Robotic Assisted Surgery Main Embodiments
Embodiment 3: Robotic Devices And Systems for Diagnosis and Treatment with Artificial Intelligence Assistance

AI and Robotic Assisted Surgery Main Embodiments
Embodiment 4: Method 3 for Determining HandlePose, PatPose

Method 3: Using Camera Arrays from VR Headset

AI and Robotic Assisted Surgery Main Embodiments
Embodiment 5: Method-5 Using FFC to Derive CamPose from HandlePose

Examples of images/Video of the cannula by the FFC

AI and Robotic Assisted Surgery Main Embodiments
Embodiment 5: Method-5 Using FFC to Derive CamPose from HandlePose

Examples of images/Video of the cannula by the FFC

AI and Robotic Assisted Surgery Main Embodiments
Embodiment 5: Method-5 Using FFC to Derive CamPose from HandlePose

Examples of images/Video of the cannula by the FFC

AI and Robotic Assisted Surgery Main Embodiments
Embodiment 5: Method-5 Using FFC to Derive CamPose from HandlePose

Examples of images/Video of the cannula by the FFC

AI and Robotic Assisted Surgery Main Embodiments
Embodiment 5: Method-5 Using FFC to Derive CamPose from HandlePose Examples of images/Video of the cannula by the FFC

HAND-HELD, ROBOTIC-ASSISTED ENDOSCOPE WITH POSITION TRACKING

REFERENCE TO RELATED APPLICATIONS

This application claims the benefit of and incorporates by reference each of the following non-provisional patent applications:

U.S. Prov. Ser. No. 63/256,634 filed Oct. 18, 2021;
U.S. Prov. Ser. No. 63/282,108 filed Nov. 22, 2021;
U.S. Prov. Ser. No. 63/283,367 filed Nov. 26, 2021;
U.S. Prov. Ser. No. 63/332,233 filed Apr. 18, 2022;

This application is a continuation-in-part of, incorporates by reference, and claims the benefit of the filing date of each of the following patent applications, as well as of the applications that they incorporate by reference, directly or indirectly, and the benefit of which they claim, including U.S. provisional applications, U.S. non-provisional and non-provisional patent applications:

U.S. Non-Prov. Ser. No. 16/363,209 filed Mar. 25, 2019;
U.S. Non-Prov. Ser. No. 17/362,043 filed Jun. 29, 2021;
U.S. Non-Prov. Ser. No. 17/473,587 filed Sep. 13, 2021;
U.S. Non-Prov. Ser. No. 17/745,526 filed May 16, 2022;
U.S. Non-Prov. Ser. No. 17/521,397 filed Nov. 8, 2021; and
U.S. Non-Prov. Ser. No. 17/720,143 filed Apr. 13, 2022

This patent application is related to and incorporates by reference each of the following international, non-provisional and provisional applications:

International Patent Application No. PCT/US17/53171 filed Sep. 25, 2017;
U.S. Pat. No. 8,702,594 Issued Apr. 22, 2014;
U.S. patent application Ser. No. 16/363,209 filed Mar. 25, 2019;
International Patent Application No. PCT/US19/36060 filed Jun. 7, 2019;
U.S. patent application Ser. No. 16/972,989 filed Dec. 7, 2020;
U.S. Prov. Ser. No. 62/816,366 filed Mar. 11, 2019;
U.S. Prov. Ser. No. 62/671,445 filed May 15, 2018;
U.S. Prov. Ser. No. 62/654,295 filed Apr. 6, 2018;
U.S. Prov. Ser. No. 62/647,817 filed Mar. 25, 2018;
U.S. Prov. Ser. No. 62/558,818 filed Sep. 14, 2017;
U.S. Prov. Ser. No. 62/550,581 filed Aug. 26, 2017;
U.S. Prov. Ser. No. 62/550,560 filed Aug. 25, 2017;
U.S. Prov. Ser. No. 62/550,188 filed Aug. 25, 2017;
U.S. Prov. Ser. No. 62/502,670 filed May 6, 2017;
U.S. Prov. Ser. No. 62/485,641 filed Apr. 14, 2017;
U.S. Prov. Ser. No. 62/485,454 filed Apr. 14, 2017;
U.S. Prov. Ser. No. 62/429,368 filed Dec. 2, 2016;
U.S. Prov. Ser. No. 62/428,018 filed Nov. 30, 2016;
U.S. Prov. Ser. No. 62/424,381 filed Nov. 18, 2016;
U.S. Prov. Ser. No. 62/423,213 filed Nov. 17, 2016;
U.S. Prov. Ser. No. 62/405,915 filed Oct. 8, 2016;
U.S. Prov. Ser. No. 62/399,712 filed Sep. 26, 2016;
U.S. Prov. Ser. No. 62/399,436 filed Sep. 25, 2016;
U.S. Prov. Ser. No. 62/399,429 filed Sep. 25, 2016;
U.S. Prov. Ser. No. 62/287,901 filed Jan. 28, 2016;
U.S. Prov. Ser. No. 62/279,784 filed Jan. 17, 2016;
U.S. Prov. Ser. No. 62/275,241 filed Jan. 6, 2016;
U.S. Prov. Ser. No. 62/275,222 filed Jan. 5, 2016;
U.S. Prov. Ser. No. 62/259,991 filed Nov. 25, 2015;
U.S. Prov. Ser. No. 62/254,718 filed Nov. 13, 2015;
U.S. Prov. Ser. No. 62/139,754 filed Mar. 29, 2015;
U.S. Prov. Ser. No. 62/120,316 filed Feb. 24, 2015; and
U.S. Prov. Ser. No. 62/119,521 filed Feb. 23, 2015.

FIELD

This patent specification generally relates to endoscopy instruments and methods. Some embodiments relate to endoscopic instruments that include a single-use portion releasably attached to a reusable portion.

BACKGROUND

Endoscopes have long been used to view and treat internal tissue. In the case of both rigid and flexible conventional endoscopes, the optical system and related components are relatively expensive and are intended to be re-used many times. Therefore, stringent decontamination and disinfection procedures need to be carried out after each use, which require trained personnel and specialized equipment and wear out the multiple-use endoscopes. In recent years, disposable endoscopes have been developed and improved, typically comprising a single-use portion that includes a single-use cannula with a camera at its distal end, releasably attached to a reusable portion that includes image processing electronics and a display. Disposable or single-use endoscopy significantly lessens the risk of cross-contamination and hospital acquired diseases and is cost-effective. Such endoscopes find applications in medical procedures such as imaging and treating the male and female urinary system and the female reproductive system and other internal organs and tissue. Examples of disposable endoscopes are discussed in U.S. Pat. Nos. 10,292,571, 10,874,287, 11,013,396, 11,071,442, 11,330,973, and 11,350,816.

Robotic and robotic-assisted surgeries have drawn much attention in industry and academia. The tend to be large-format, specialized systems that require specialized surgical suites, tend to be cumbersome to set up, and tend to have limited flexibility.

This parent specification is directed to systems of a different type—small-format, hand-held and modular, with digital integration and artificial intelligence to enable robot-assisted procedures that do not need specialized surgical suits and can be used in a doctor's office, and provide significant enhancement compared to endoscopic systems without robotic assistance. This specification is directed to endoscopic systems that can be efficaciously used with or without enabling one or more of the available robotic assistance facilities.

The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

SUMMARY

As described in the initially presented claims but subject to amendments thereof in prosecuting this patent application, according to some embodiments a compact, robotic-assisted endoscopic system comprises: an endoscope comprising a single-use portion that includes a cannula with a camera at a distal end thereof and a reusable portion to which the single-use portion is releasably coupled to form the endoscope; a first transducer arrangement mounted to at least one of the reusable and single-use portion and configured to derive measures of relative position of a selected part of the single-use portion relative to the reusable portion; wherein the first transducer arrangement is configured to operate in one or more of the following modalities to track motion of the single-use portion relative to the reusable portion or another coordinate system: laser tagging using time of flight; ultrasound positioning using time of flight; imaging at least one of the single-use and reusable portions with a VR headset with camera arrays; RF tracking of a selected part of the single-use portion; driving said cannula in selected motion with multiple degrees of freedom with step motors and tracking said motion by step motors operating parameters; tracking motion of the single-use portion with forward facing camera system (FFC) mounted to the reusable portion; FFC tracking of reflective tags arranged on the single-use portion; and FFC tracking of LLDs arranged on the single-use portion; N the system further comprises a processor receiving outputs of said first transducer arrangement related to said tracking and configured to derive therefrom CamPose coordinates of a selected part of the single-use portion relative to the reusable portion or relative to another coordinate system; and a display configured to display images of an object being diagnosed or treated with said endoscope juxtaposed with images of said distal part of the single-use portion.

According to some embodiments, the system can further include one or more of the following features: (a) further including a second transducer arrangement configured to measure HandlePose indicative of at least one of a position and orientation of the reusable portion relative to a selected coordinate system; (b) at least a part of the second transducer is housed in said VR headset and is configured to measure HandlePose relative to the VR headset; (c) at least a part of the second transducer arrangement is mounted at a selected position that does not change with movement of said endoscope and the second transducer arrangement and is configured to measure HandlePose relative to said selected position; and (d) including a source of guidance images related to a medical procedure on said object or like objects, including prior images of the object, standard images related to the object, and/or tutorial information related to the medical procedure.

According to some embodiments, a compact, hand-held, robotic-assisted endoscopic system comprises: an endoscope comprising a single-use portion that includes a cannula with a camera at a distal end thereof and a reusable portion to which the single-use portion is releasably coupled to form the endoscope; a manual control at the reusable portion configured to be operated by a user grasping the reusable portion and to control rotation and translation of at least a part of the single-use portion relative to the reusable portion and angulation of a distal part of the single-use portion relative to a long axis thereof; a display coupled with said camera and configured to display currently taken images of an object taken with the camera concurrently with additional images that comprise one or more of prior images of the object, images of like objects, and images for guiding a medical procedure on the object; a motorized control of one or more of the motions of at least some of the single-use portion relative to the reusable portion; and a processor configured to supply said display with said additional images and to selectively drive said motorized control.

The system described in the immediately preceding paragraph can further include one or more of the following features: (a) including a first tracking arrangement configured to automatically provide an estimate of at least one of a varying position and varying orientation of a part of the single-use portion relative to the reusable portion and a processor configured to use said estimate in showing on said display a current image of said part of the single-use portion relative to said object; (b) said first tracking arrangement comprises a radio frequency (RF) transmitter at the distal end of the cannula and an RF receiver on the reusable portion; and (c) the first tracking arrangement comprises causing said processor to derive said estimate based at least in part on signals related to said motorized control driving said single-use portion relative to the reusable portion.

According to some embodiments, a compact, hand-held endoscopic system comprises: an endoscope comprising a single-use portion that includes a cannula with a camera at a distal end thereof and a reusable portion to which the single-use portion is releasably coupled to form the endoscope; a manual control at the reusable portion configured to be operated by a user grasping the reusable portion and to control rotation and translation of at least a part of the single-use portion relative to the reusable portion and angulation of a distal part of the single-use portion relative to a long axis thereof; a display coupled with said camera and configured to display currently taken images of an object taken with the camera concurrently with additional images that comprise one or more of prior images of the object, images of like objects, and images for guiding a medical procedure on the object; and a processor configured to supply said display with said additional images and to selectively drive said motorized control.

According to some embodiments, the system described in the immediately preceding paragraph can further include a scan mode or operation in which the manual control is configured to respond to a single push to cause a distal part of the reusable portion to rotate through a predefined angle around a long axis of the single use portion while angulated relative to said long axis to thereby automatically scan a predetermined interior area of the object.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

DETAILED DESCRIPTION

Figure 1:
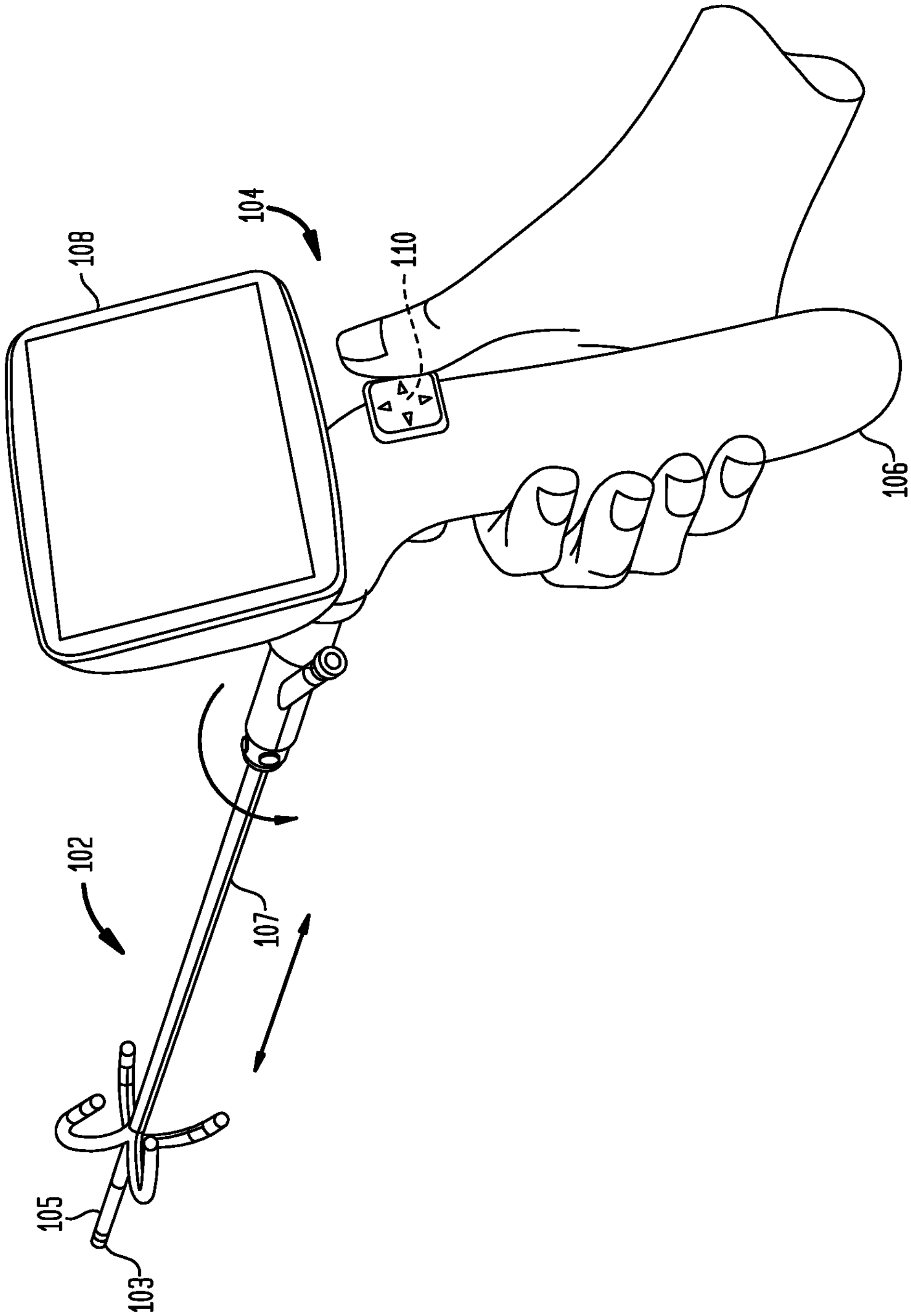
FIG. 1 is a perspective view of a compact robotic system, according to some embodiments.

A detailed description of examples of preferred embodiments is provided below. While several embodiments are described, the new subject matter described in this patent specification is not limited to any one embodiment or combination of embodiments described herein, but instead encompasses numerous alternatives, modifications, and equivalents. In addition, while numerous specific details are set forth in the following description to provide a thorough understanding, some embodiments can be practiced without some or all these details. Moreover, for the purpose of clarity, certain technical material that is known in the related art has not been described in detail to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

This patent specification describes endoscopy systems with functionalities enhanced or augmented with different degrees and kinds of robotic and artificial intelligence (AI) assistance in varying but related embodiments. Clinicians can still directly manually control an endoscope and associated devices but some of the movements or actions are assisted by power-driven robotic control and AI. The new systems described in this patent specification augment human operator performance by combining human skill and judgment with the precision and artificial intelligence of robotic assistance. The systems described in this patent specification require significantly less capital equipment than known full-scale robotic surgery equipment and relatively minimal set-up or special rooms, and optimally combine clinician skills and a degree of robotic assistance for efficient and efficacious outcomes.

The functionalities of the new systems include:

- 3D or stereoscopic vision using multiple cameras from different viewpoints
- Feedback through sight cameras for precise control of cannulas of catheters
- Motor-driven or manual 3D motions: articulations (angulations), translations, and rotations of components
- Ergonomic arrangement of hand-held instruments in which the user's hands are in a natural forward position and the hands and the instrument are within the natural vision field
- Magnification of images, for example 5×, facilitating more precise and smoother positioning of instruments or components
- Multi-frame and multi-spectra facilitating differentiation of tissue structure and nature
- Use of data from many prior images and procedures for real-time recognition, analysis, and guidance to assist in procedure planning and execution and enhance dexterity
- Small format and portable, hand-held configurations to allow procedures away from specialized operation rooms
- Modular design to enable multiple configurations and use of multiple small-format robotic-assisted endoscopes to combine different capabilities or uses in a single procedure for more complex surgeries or other visualization or treatments As described in more detail below, one of the important aspects of the new endoscopic system is that the user such as a surgeon, a urologist, or a gynecologist in in contact with or immediately next to the patient and typically hold the endoscope during the procedure, in contrast to known full-size robotic surgery systems in which the user typically is at a console or a microscope spaced from the patient and does not actually hold the instruments that go into the patient.

FIG. 1 illustrates a compact, hand-held, robotic assisted endoscopic system according to some embodiments. Endoscope 100 comprises a single-use portion 102 that includes a cannula 107 with a camera and light source module 103 at its distal end thereof and a reusable portion 104 that includes a handle 106 and a display 108 that typically displays images acquired with the camera and/or other information such as patient and procedure identification and other images. Module 103 can comprise two or more image sensors that can serve as independent cameras to provide stereo or 3D views. As indicated by arrows, cannula 107 is configured to rotate and translate relative to reusable portion 104 and a distal part 105 of cannula 107 is configured to angulate relative to a long axis of the cannula 107. Handle 106 typically includes controls such buttons, joystick and/or touch pad 110 through which the user can control angulation, rotation and/or translation of the distal and or other parts of the single-use portion, for example with the thumb of the hand holding handle 106. Distal part 105 of single-use portion 102 can articulate to assume positions such as illustrated in addition to being straight along the long axis of cannula 107. The illustrated robotic-assistance endoscope augments human operator performance by combining human skill with the precision and artificial intelligence of robotic facilities, as described in more details below.

Figure 2:
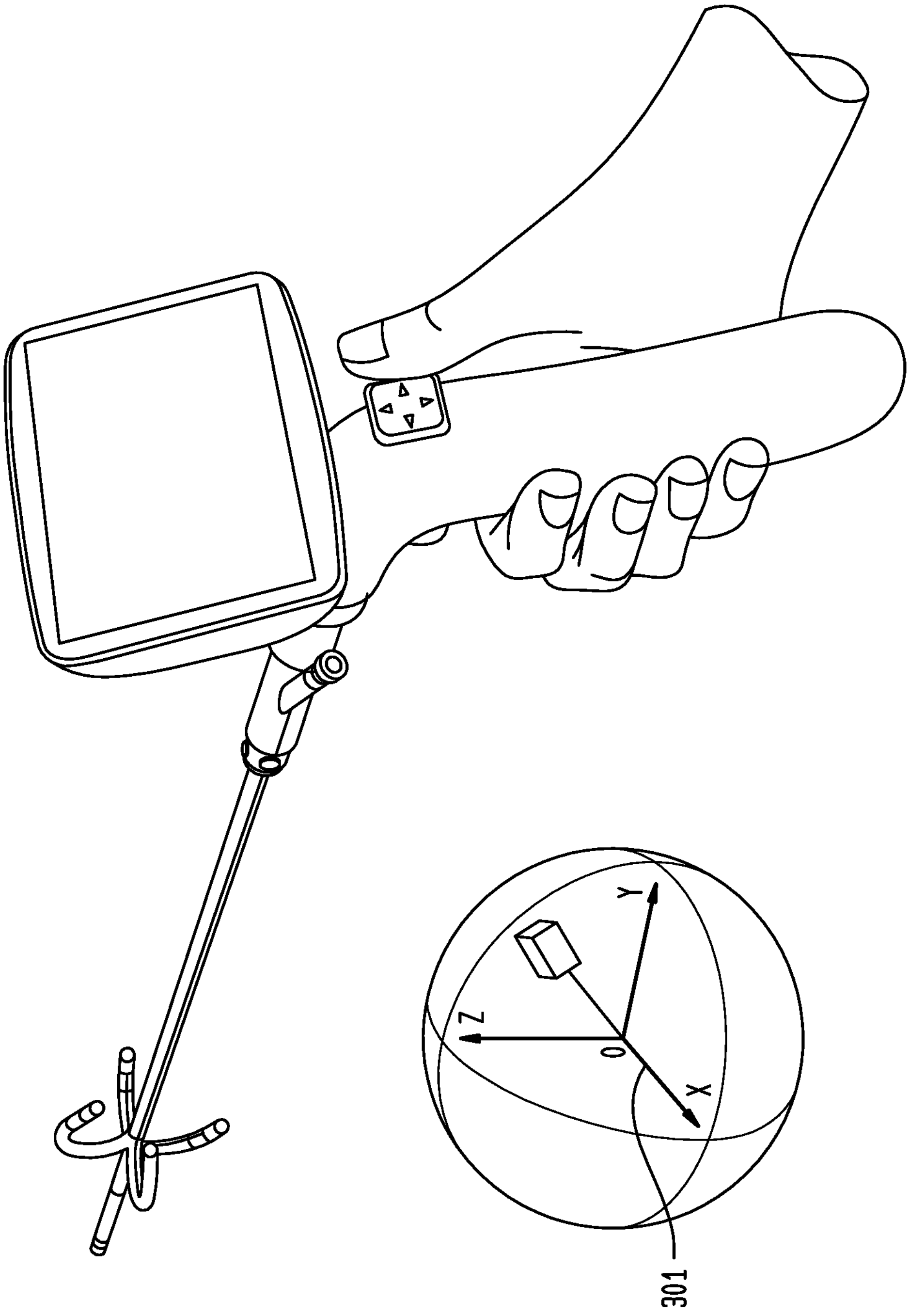
FIG. 2 illustrates definitions of coordinate systems for a compact robotic system and an object such as a patient's organ or tissue, according to some embodiments.

Endoscope 100 can be as illustrated in FIG. 1 or can be any one of the endoscopes shown and described in said patents and applications incorporated by reference herein or can comprise combinations of their features, or can be the endoscope without a display shown in FIG. 2, or a like variation thereof. Display 108 can have one or more distally- or forward-facing cameras FCC whose field or view includes distal end 105 of reusable portion 102, as discussed in more detail further below. Module 103 at the distal end of cannula 107 can comprises one or more cameras that selectively image different ranges of light wavelengths and the light source such as LEDs in module 103 can selectively emit light in desired different wavelength ranges. Endoscope 100 can include permanently mounted surgical devices such as a grasper, and injection needle, etc. and, can include a working channel through which surgical devices can be inserted to reach object 301, and can include fluid channels through which fluids can be introduced into or withdrawn from object 301, as described in said patents and applications incorporated by reference herein.

FIG. 2 illustrates definitions of positions and orientations of parts of an endoscope such as that of FIG. 1 and an object such as an internal organ or tissue of a patient, relative to coordinate systems. As illustrated in FIG. 2, the position of an object 301 can be defined in orthogonal coordinates and the object's orientation can be defined in polar coordinates, thus providing six degrees of freedom. The term PatPose in this patent specification refers to the position and/or orientation of the object at a given time. Single-use portion 102 typically has one or more cameras at its distal end and the position and/or orientation thereof are defined in the respective coordinate systems at a time and are referred to as CamPose. The position and/or orientation of reusable portion 104 or handle 106 are defined in the respective coordinate systems at a time and are referred to as HandlePose.

Figure 3:
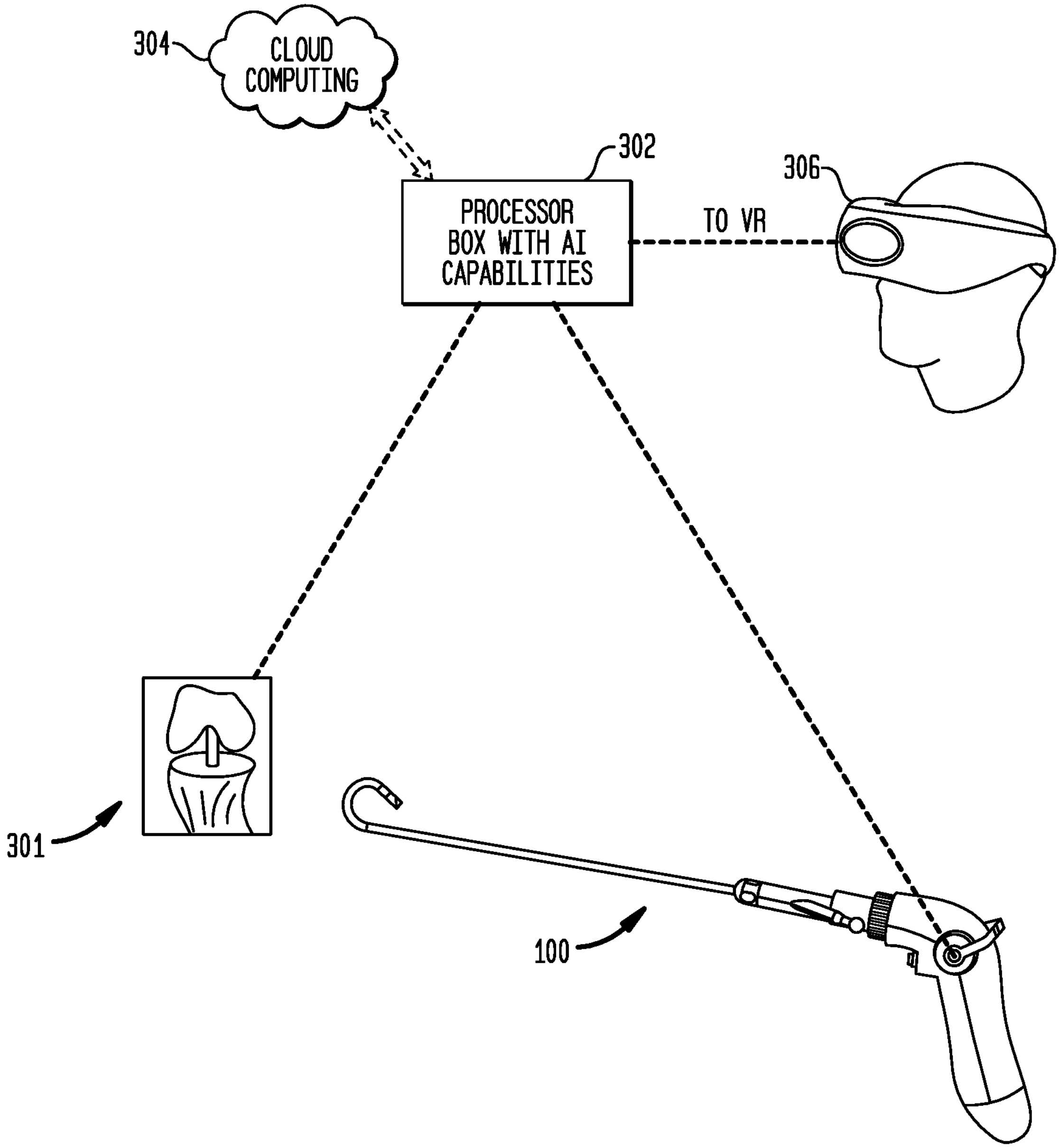
FIG. 3 illustrates AI and robotic assisted surgery using a compact robotic system involving fusion of real time information from internal and external sensors and the use of an AI engine and a virtual reality headset, according to some embodiments.

FIG. 3 illustrates an endoscope such as that of FIG. 1 but without display 108, in a medical procedure imaging and/or treating object 301, according to some embodiments. Object 301 can be a patient's knee joint, as illustrated, or another organ or tissue, such as a patient's bladder, uterus, spine, etc. In this example the procedure makes use of real-time information from internal and external sensors at endoscope 100, a processor 302 with AI capabilities, a cloud computing source 304, and a virtual reality (VR) headset 306 such as an adaptation of a commercially available model, for example Oculus Quest 2, HTC Vive Pro 2, HTC Vive Cosmos Elite, or HP Reverb G2. HandlePose information can be provided in real or near real time using techniques such as laser tagging, ultrasound imaging or detection, and camera tracking via VR headset 306. CamPose information can be obtained in real or near real time using techniques such as radio frequency (RF) tracking of the single-use portion 102, including its distal portion 105, or as derived from HandlePos information and the known statial relationship between the single-use and reusable portions and commanded articulation, rotation and translation, of by a combination of the two aforesaid techniques. The illustrated system is configured to supply the CamPose and HandlePose information to a processor 302 with AI capabilities that can communicate with VR headset 306 and with cloud computing facility 304 that can supply information such as from a database of prior procedures and guidance for the current procedure. Processor 302 communicates with VR headset 306, typically wirelessly, as currently done in commercially available videogame systems.

Figure 4:
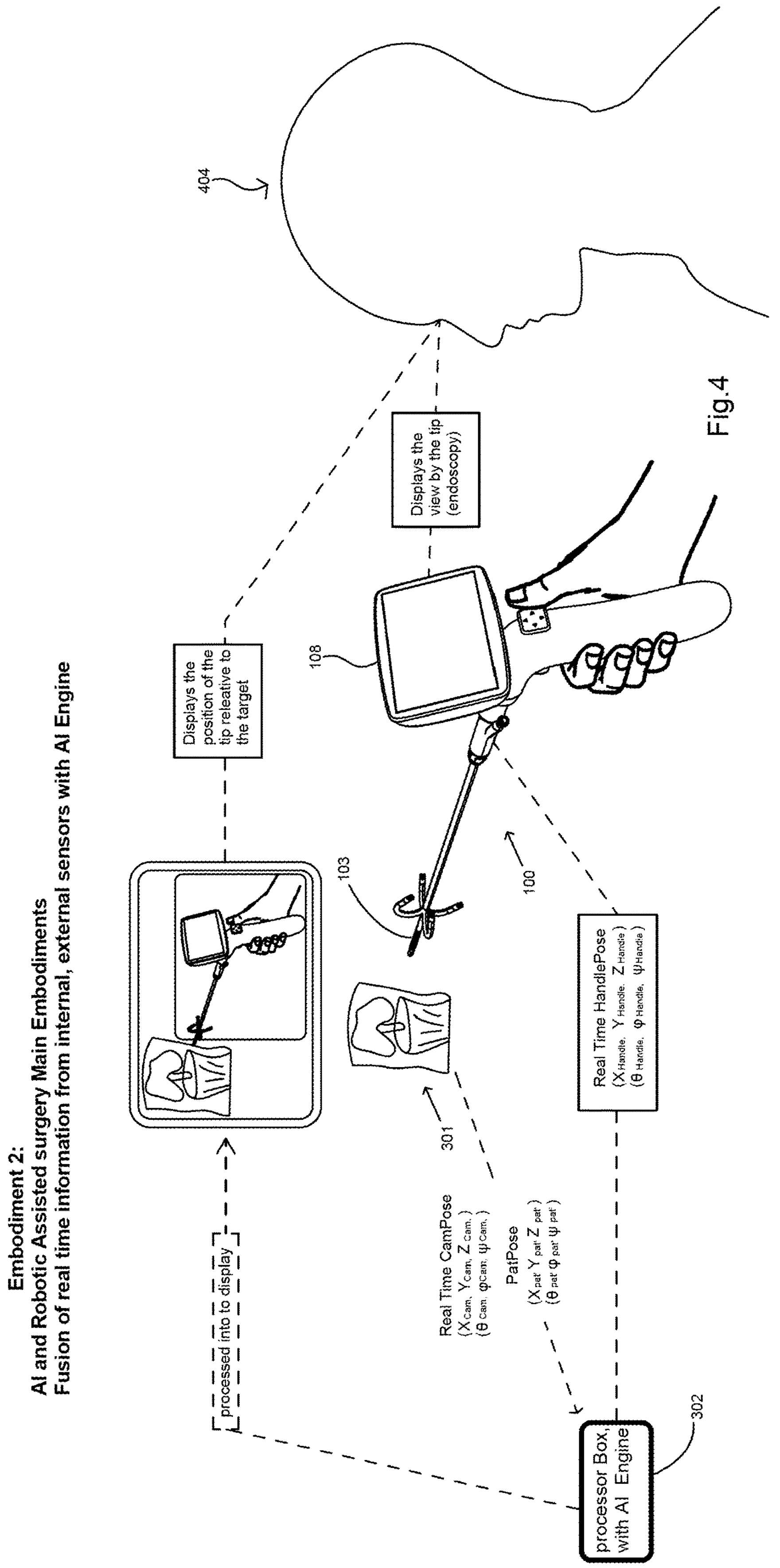
FIG. 4 illustrates AI and robotic assisted surgery using a compact robotic system involving fusion of real time information from internal and external sensors and the use of an AI engine, according to some embodiments.

FIG. 4 illustrates AI-assisted imaging and/or surgery involving fusion of real-time information from internal and external sensors with AI engine facilities, according to some embodiments. Endoscope 100, with display 108, can be as in FIG. 1 and views and/or treats object 301. In addition, a typically larger-format display 402 can be driven, preferably wirelessly, by processor 302 to display information such as images of the distal part 105 or camera 103 of single-use portion and object 301 and their relative positions and orientations, and/or other information. User 404 can view display 108 and/or display 402 as needed during a medical procedure. As described in connection with FIG. 2, endoscope 100 supplies real-time CamPos and HandlePos information to processor 302, preferably wirelessly. In this example, processor 302 supplies display 402 with processed information for the display of images such as images showing the distal part 105 of single-use portion 102, camera 103, object 301, the relative positions thereof, and/or other information.

Figure 5:
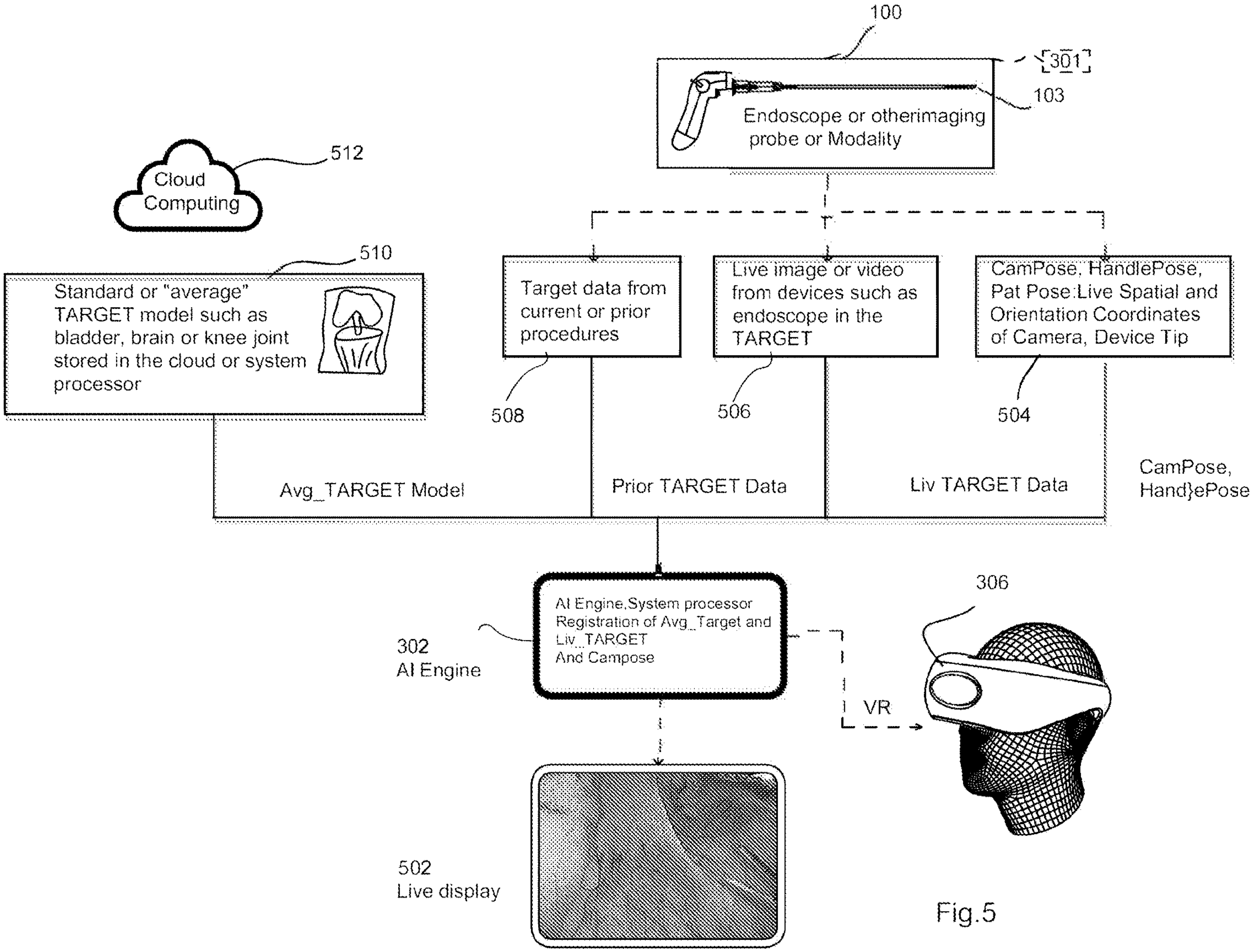
FIG. 5 illustrates AI and robotic assisted surgery involving use of robotic devices and systems for diagnosis and treatment with AI assistance, according to some embodiments.

FIG. 5 illustrates robotic devices and systems for diagnosis and treatment with artificial intelligence assistance. Endoscope 100 or another imaging modality of probe provides images of an object 301 taken with a camera at the endoscope's distal end. Input/output (I/O) device 504 assembles position and/or orientation information CamPose and HandlePose as described above and supplies that information to AI engine and system processor 302. I/O unit 506 assembles live images or video of object 301 taken with camera module 103 of endoscope 100 or another probe or with another modality and supplies the resulting Liv_TARGET Data to unit 302. Database unit 508 stores data such as prior images of object 301 taken in prior medical procedures on the same patient or taken earlier in the same procedure and supplies them to unit 302. I/O and database unit 510 provides to unit 302 data such as images and/or other parameters desaignated Avg_TARGET Model that have been derived from or are about objects like object 301, derived for example from a collection of such images and/or parameters acquired from a typically large population of patients and possibly from other sources such as anatomy reference material. Some of or all the information for Avg_TARGET Model may come from an Internet or other connection with a cloud computing source 512. AI Engine and System Processor 302 processes the information supplied thereto from units 504, 506, 508, and 510 to generate live images and/or video of object 301 and endoscope 100 (including its distal end 105 and module 103) and/or images/video of average or typical objects 301 and/or of and displays the images/video at a display 502 and/or VR headset 306.

Figure 6:
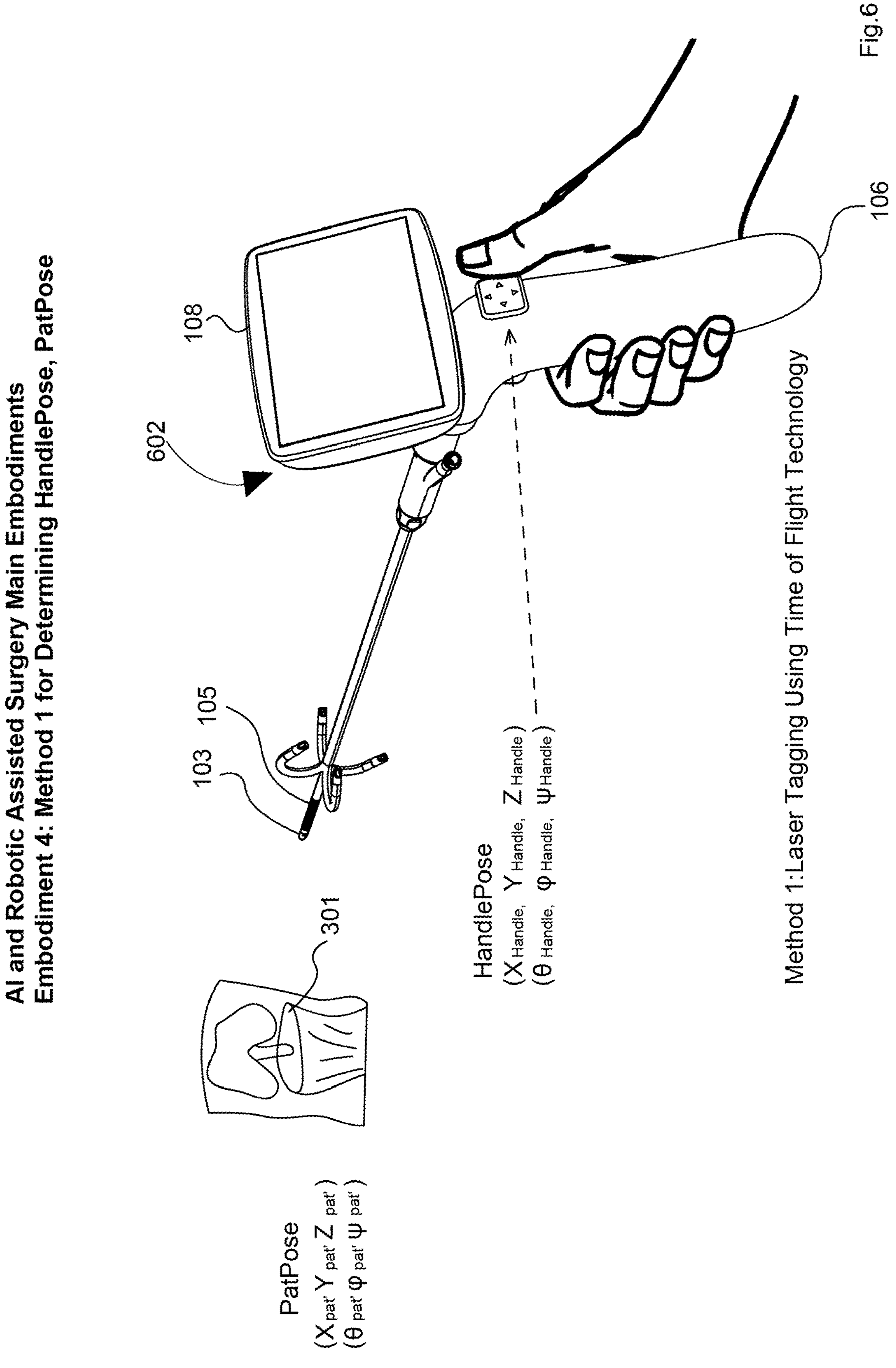
FIG. 6 illustrates AI and robotic assisted surgery involving determining HandlePose and PatPose parameters by laser tagging and time of flight technology, according to some embodiments.

In a medical procedure with the system of FIG. 5, the images displayed at units 306 and 502 can guide the user in inserting single-use portion 102 toward object 301 and during a medical procedure, by showing at the user's choice material such as a real time view of the relative positions and orientations of the distal end of cannula 107 (and any surgical devices protruding therefrom) and object 301, images or video of object 301 taken earlier in the procedure, how object 301 would or should be seen (including portions of object 301 that are not currently in the field of view of endoscope 100) and how similar procedures have been performed based on information provided by Avg_TARGET Model. If some of the motions of single-use portion 102 and surgical devices protruding therefrom are motor-controlled, the information from unit 302 can be used to augment manual control of such motions. For example, information from unit 302 can limit the extent of angulation of distal part 105 of cannula 107 if analysis by unit 302 of images taken of object 301 indicate that motion commanded manually is not consistent with the current environs of part 105 in object 301. As another example FIG. 6 illustrates determining HandlePose and PatPose (position and/or orientation of reusable portion 104 and object 301) using laser time-of-fight technology. PatPose relative to handle 106 can be determined using laser illumination of object 301 with laser light emitted from module 103 or from distal part 105 of single-use portion 102 and/or from a laser source 602 at the distally facing side of display 108. The arrangement of FIG. 6 can be used as endoscope 100 in the system of FIG. 5, or as a stand-alone arrangement. Position and/or orientation of handle 106 and/or a portion single-use portion 102 that is not in a patient can be determined relative to a fixed frame of reference using one or more laser sources and imagers 604 at fixed positions such as on room walls illuminating handle 106. FIG. 6 shows notation for orthogonal and polar parameters for position and orientation of PatPose and HandlePose. Technology for laser time-of-flight measurements is known, for example as discussed in https://www.terabee.com/time-of-flight-principle/ and https://en.wikipedia.org/wiki/Time-of-flight_camera, incorporated herein by reference.

Figure 7:
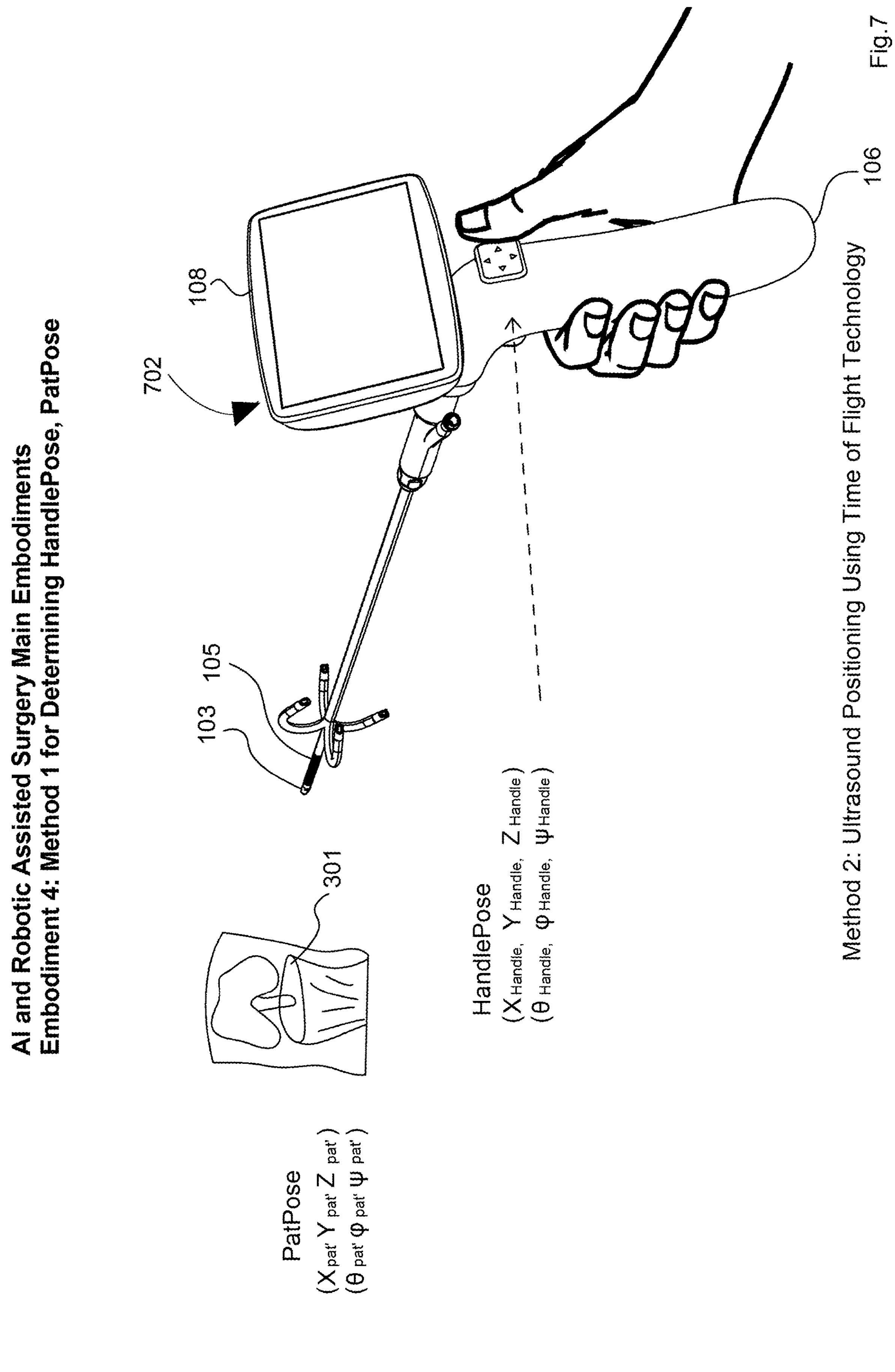
FIG. 7 illustrates AI and robotic assisted surgery involving determining HandlePose and PatPose parameters by ultrasound technology, according to some embodiments.

FIG. 7 is otherwise like FIG. 6 but illustrates determining HandlePose and PatPose using ultrasound time-of-flight technology, for example with ultrasound transducers mounted at distal tip 105, display 108, and/or at fixed locations 702 such on room walls or ceiling. The arrangement of FIG. 7 can be used as endoscope 100 in the system of FIG. 5, or as a stand-alone arrangement. Technology for ultrasound time-of-flight measurements is known, for example as discussed in https://www.terabee.com/time-of-flight-principle/.

Figure 8:
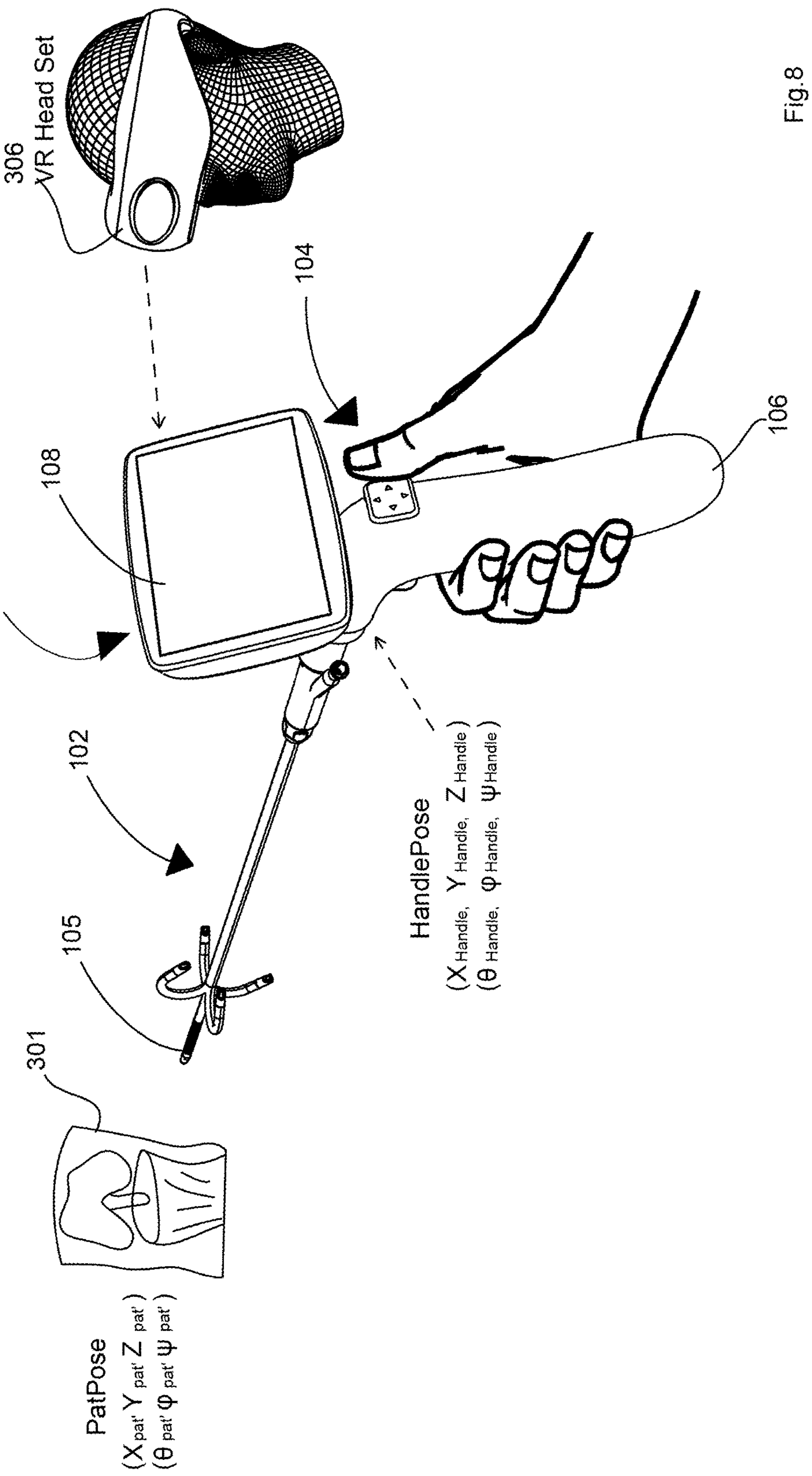
FIG. 8 illustrates AI and robotic assisted surgery involving determining HandlePose and PatPose parameters using camera arrays at a VR headset, according to some embodiments.

FIG. 8 illustrates and arrangement determining HandlePose and PatPose using camera arrays in VR headset 306. For example, a commercially available VR headset shown at https://www.hp.com/us-en/shop/pdp/hp-reverb-g2-virtual-reality-headset?&a=1&jumpid=cs_con_nc_ns&utm_medium=cs&utm_source=ga&utm_campaign=HP-Store_US_All_P-S_All_Hgm_OPEX_Google_ALL_Smart-PLA_Accessories_UNBR&utm_content=sp&adid=600244346557&addisttype=u&1G5U1AA%23ABA&cq_src=google_ads&cq_cmp=17340334760&cq_con=142804800851&cq_term=&cq_med=&cq_plac=&cq_net=u&cq_pos=&cq_plt=gp&qclid=Cj0KCOjw9ZGYBhCEARIsAEUXITW5Ep4EG1m8Q7b6guathK9zTOvjdZd2UhA7FVn4LubtKhuYOpccCigaAl9sEALw_wcB&gclsrc=aw.ds can serve at VR headset 306 to track movement of single-use portion 102 and reusable portion 104 in real time. If needed, markers for tracking can be secured at pertinent locations on portions 102 and 104. HandlePose can be determined relative to a fixed coordinate system with transducers, e.g., ultrasound or light or RF transducers 802 on room walls or ceiling.

Figure 9:
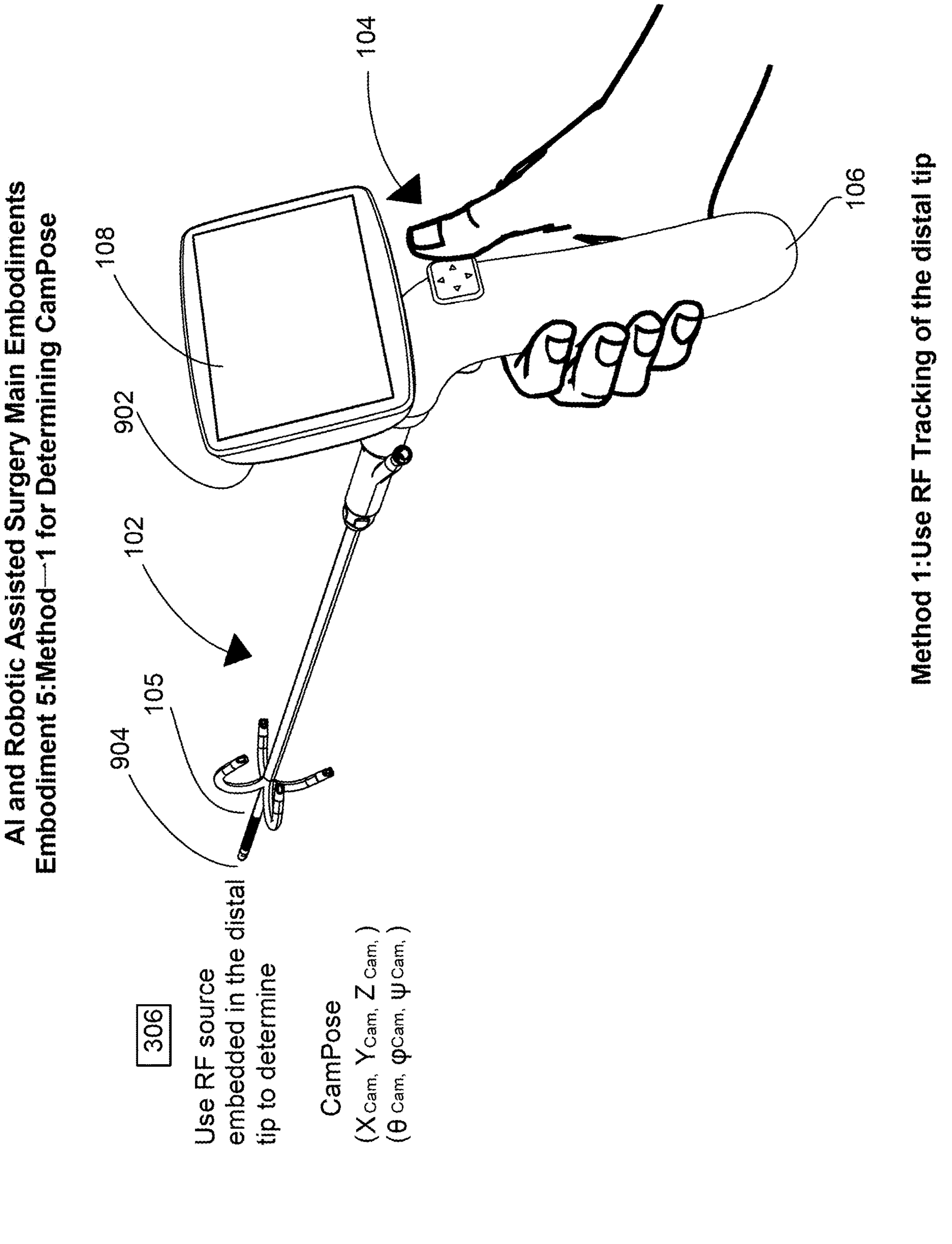
FIG. 9 illustrates AI and robotic assisted surgery involving determining HandlePose and PatPose parameters by RF tracking, according to some embodiments.

FIG. 9 is otherwise like FIG. 6 but illustrates use of RF (radio frequency) tracking of CamPose. In this example, one or more radio frequency receivers 902 are secured to reusable portion 104, for example at the distally facing surface of display 108, to receive a radio frequency transmission from a source 904 at the tip of distal part 105 of single-use portion 102. The indicated CamPose information can show in real time where the distal top of cannula 107 is located relative to reusable portion 104, including after translation of cannula 107 along its long axis relative to handle 106. The arrangement of FIG. 9 can be used as endoscope 100 in the system of FIG. 5, or as a stand-alone arrangement. Technology for RF distance measurements is commercially available, see for example https://www.researchgate.net/publication/224214985_Radio_Frequency_Time-of-Flight_Distance_Measurement_for_Low-Cost_Wireless_Sensor_Localization. If needed, markers for tracking can be secured at pertinent locations on portions 102 and 104. HandlePose can be determined relative to a fixed coordinate system with transducers, e.g., ultrasound or light or RF transducers 802 on room walls or ceiling.

Figure 10:
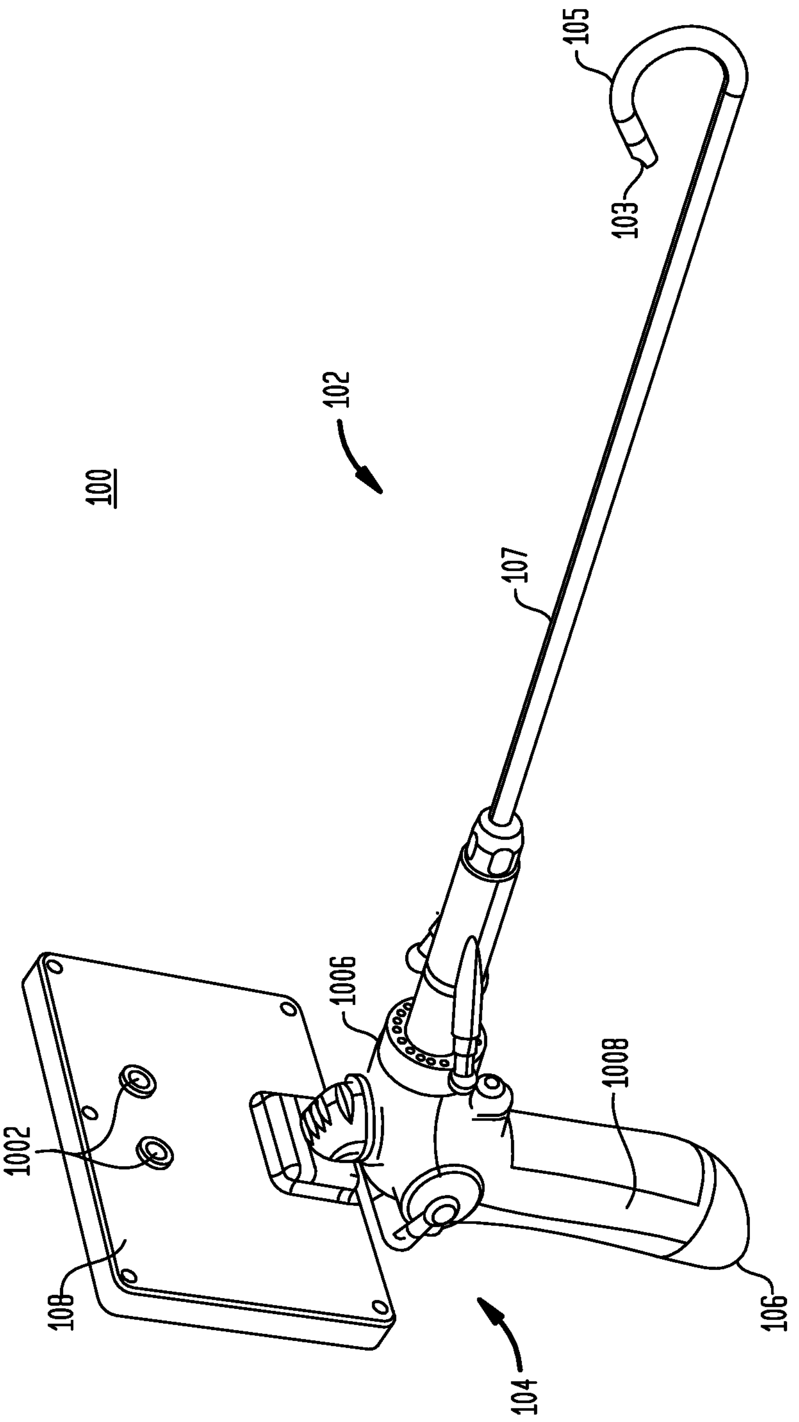
FIG. 10 illustrates AI and robotic assisted surgery involving determining HandlePose and PatPose parameters step motors operation, according to some embodiments.

FIG. 10 illustrates using one or more step motors to derive CamPose relative to HandlePose. Endoscope 100 in the example includes two spaced-apart, forward-facing cameras (FFC) 1002 with respective light sources at the distally facing side of display 108. Digital step motors 1006 inside reusable portion 104 drive rotation and translation of cannula 107 relative to handle 106 and deflection or angulation of the distal part 105 of cannula 107. The arrangement of FIG. 10 can be used as endoscope 100 in the system of FIG. 5, or as a stand-alone arrangement. FFC 1002 view cannula 107, including its distal part 105. Step motors 1006 supply motor step signals to a processor 1008 in reusable portion 104 that is configured to determine, from a count of steps of the respective motors, the position and/or orientation of cannula 107, including its distal part 105 and tip. FFC 1002 generate real time images of cannula 107 and its distal portion 105 and tip that also are fed to processor 1008, which is configured to correlate these images with step motor counts to determine CamPose relative to reusable portion 104. If HandlePose is desirable, it can be determined as discussed above for other examples, and from that CamPose can be determined relative to a selected frame of reference in addition to relative to handle 106.

Figure 11:
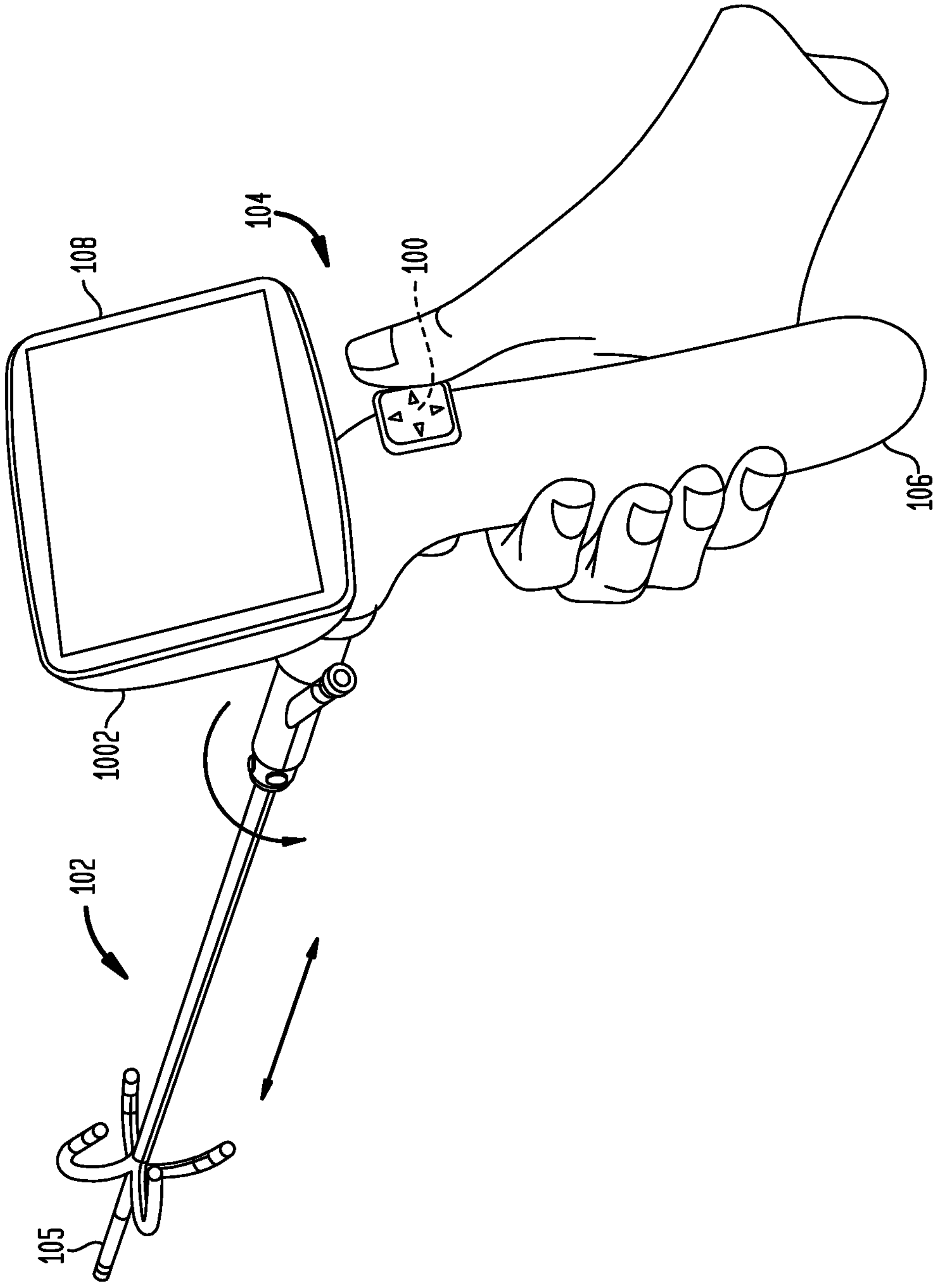
FIG. 11 illustrates AI and robotic assisted surgery involving determining HandlePose and PatPose parameters using forward facing cameras on an integral display, according to some embodiments.

FIG. 11 is otherwise like FIG. 10 but shows endoscope 100 (compact robotic system) from a different viewpoint. As with the FIG. 10 arrangement, rotation, translation and/or angulation of cannula 107 and distal part 105 relative to reusable portion 104 can be derived from the number of steps step motors 1006 (shown in FIG. 10) execute in response to manual operation of touch panel or joystick 110 (or commanded for robotic operation by unit 302 (FIG. 5)), and determination of CamPose can be further assisted with information from FFC 1002, processed in processor 1008 (shown in FIG. 10). HandlePose can be determined as discussed above for other examples. The arrangement of FIG. 11 can be used as endoscope 100 in the system of FIG. 5, or as a stand-alone arrangement.

Figure 12:
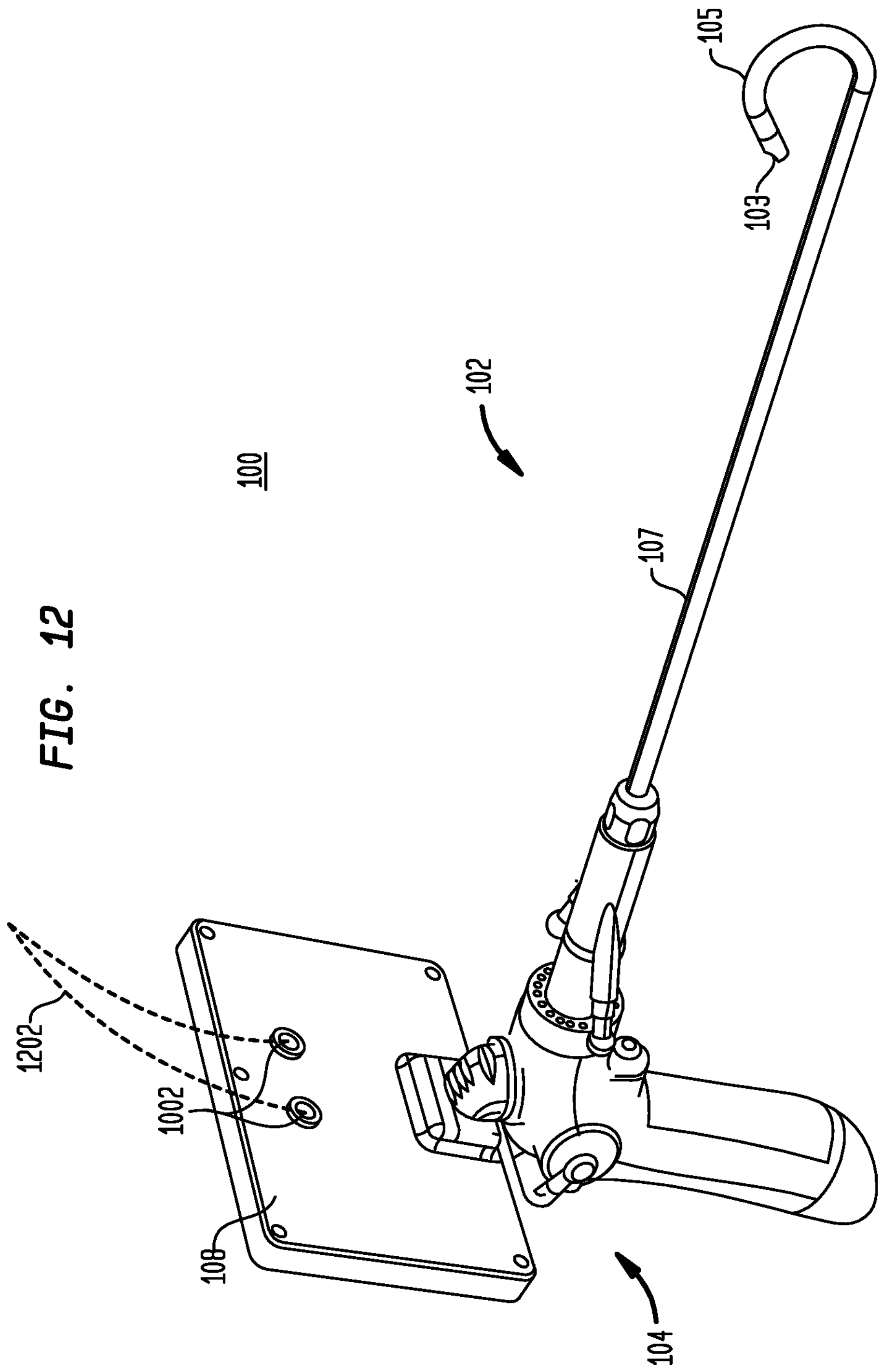
FIG. 12 illustrates AI and robotic assisted surgery involving determining HandlePose and PatPose parameters using infrared tracking, according to some embodiments.

FIG. 12 illustrates using FFC and LED to determine motion of cannula 107 and its distal part 105 relative to reusable portion 104. In other respects, the FIG. 12 arrangement is like that of FIGS. 10 and 11. In FIG. 12, reference numeral 1202 designates FFCs and their distally facing light sources. The light sources of FFc 1002 can be turned OFF in this example. A matrix 1204 of LEDs emitting infrared light can be placed at selected locations on single-use portion 102, such as along cannula 107 and its distal part 105. CamPose relative to reusable portion 104 can be derived from the images of the infrared sources along single-use portion acquired with FFC 1002 using geometric calculations based on the locations of the images of LEDs 1204 in the field of view of FFC 1202. The outputs of FCC 1002 are processed by processor 1008 (FIG. 10) as described above. HandlePose can be derived as discussed above for other examples. The arrangement of FIG. 12 can be used as endoscope 100 in the system of FIG. 5, or as a stand-alone arrangement.

Figure 13:
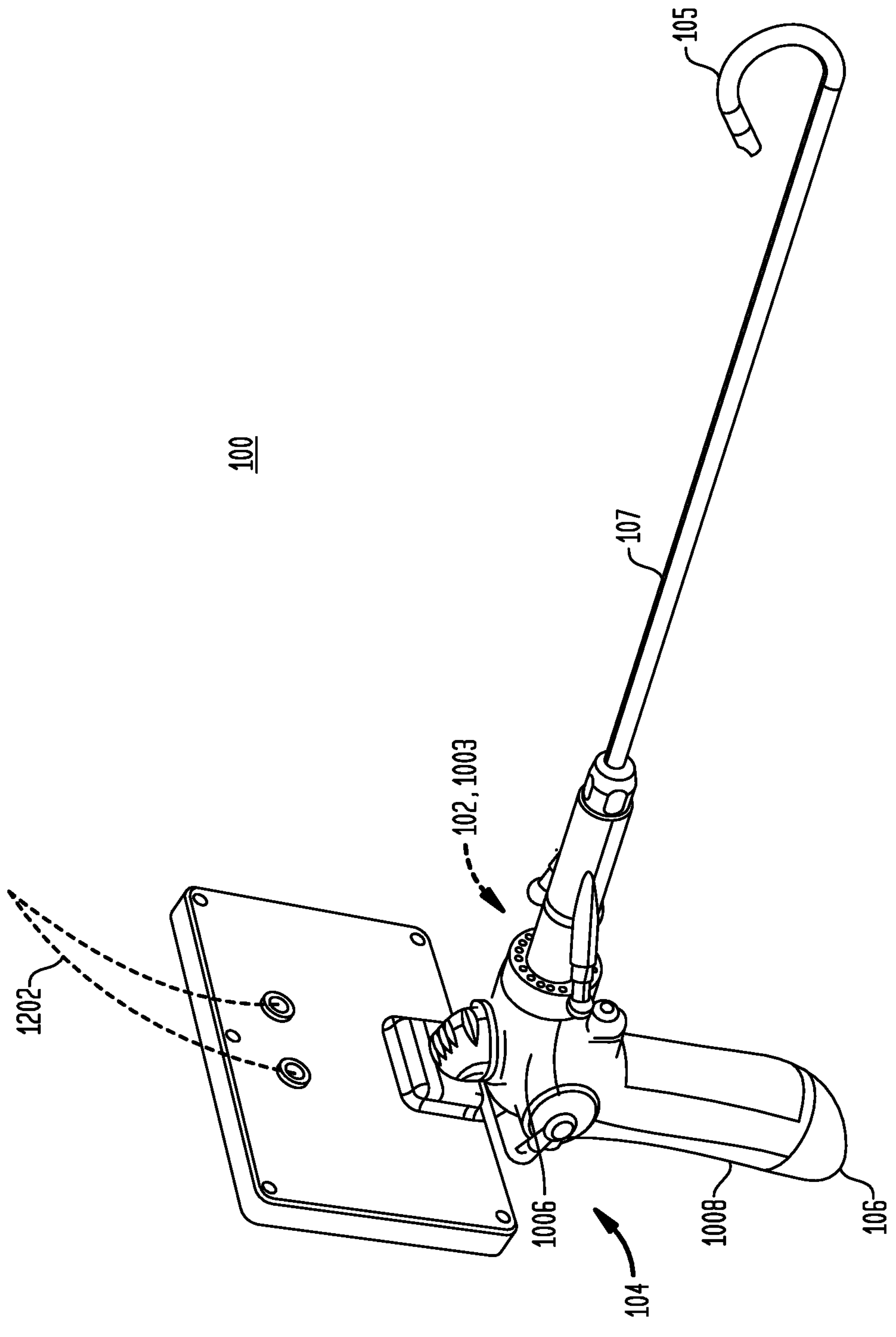
FIG. 13 illustrates AI and robotic assisted surgery involving determining HandlePose and PatPose parameters using forward facing cameras and infrared light illuminating a cannula with reflective tags, according to some embodiments.

FIG. 13 is otherwise like FIG. 12 but uses a matrix of tags 1302 along single-use portion 102, including cannula 107 and distal part 105, that reflect light from the light sources at FFC 1002.

Figure 14:
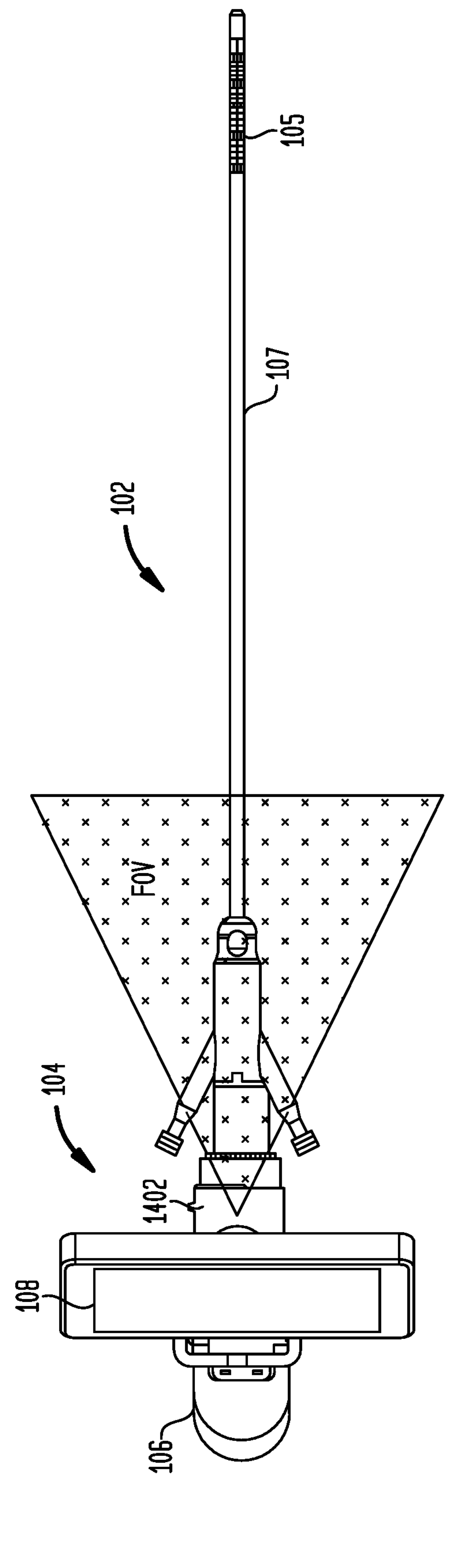
FIG. 14 illustrates AI and robotic assisted surgery involving use of forward facing cameras to determine PatPose from HandlePose, according to some embodiments.

FIG. 14 illustrates an arrangement using FCC 1402 to derive CamPose from or relative to HandlePose. In this example, one or more FCC 1402 that include respective white light sources ate on display 108 and illuminate a field of view FOV that includes cannula 107. FFC 1402 image this FOV to detect motion of cannula 107 and/or distal part 105 and derive therefrom CamPose relative to reusable portion 104 by processing the images in processor 1008 (FIG. 10). This avoids a need for reflective tags or LEDs along single-use portion 102. HandlePose can be determined as discussed above for other examples. The arrangement of FIG. 11 can be used as endoscope 100 in the system of FIG. 5, or as a stand-alone arrangement. The arrangement of FIG. 14 can be used as endoscope 100 in the system of FIG. 5, or as a stand-alone arrangement.

Figure 15:
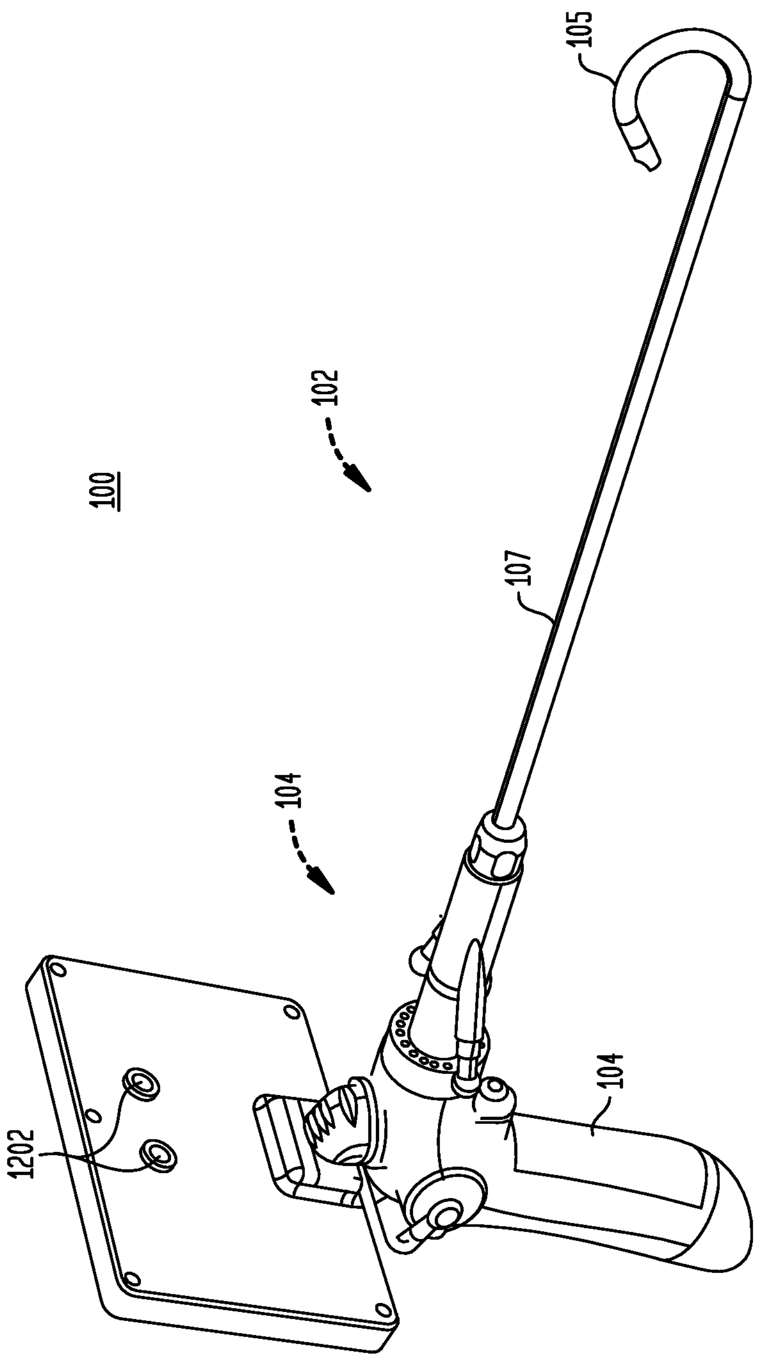
FIG. 15 illustrates an example of a view of forward facing cameras relating to determining PatPose from HandlePose, according to some embodiments.

FIG. 15 is a perspective view of a complete endoscope using FCC 1202 to derive CamPose from HondlePose as discussed above for FIG. 14.

Figure 16:
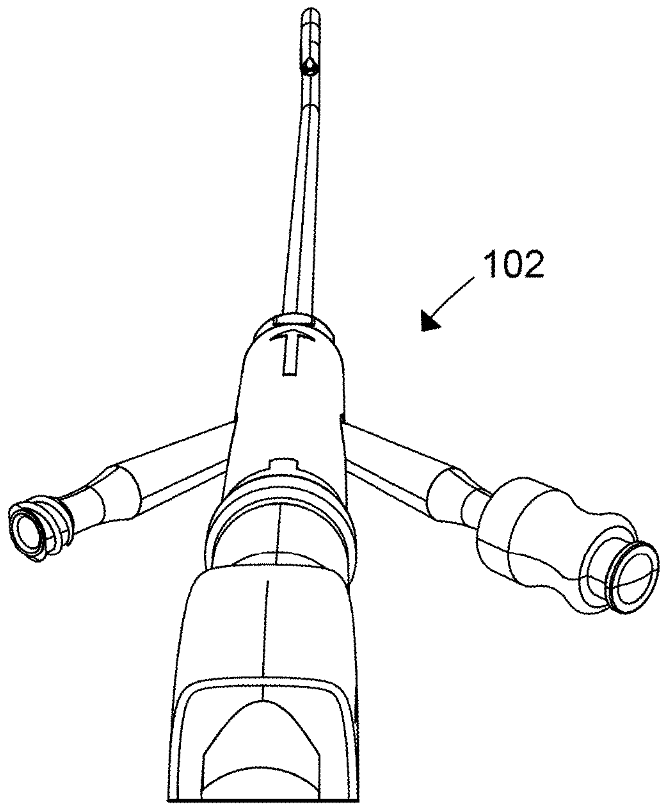
FIG. 16 illustrates an example of a view of forward facing cameras relating to determining PatPose from HandlePose, according to some embodiments.
Figure 17:
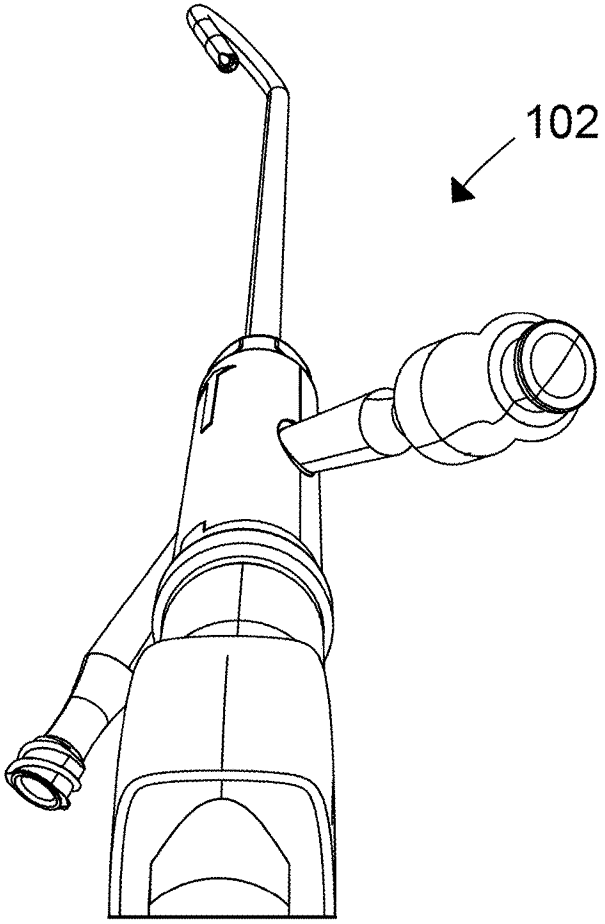
FIG. 17 illustrates another example of a view of forward facing cameras relating to determining PatPose from HandlePose, according to some embodiments.
Figure 18:
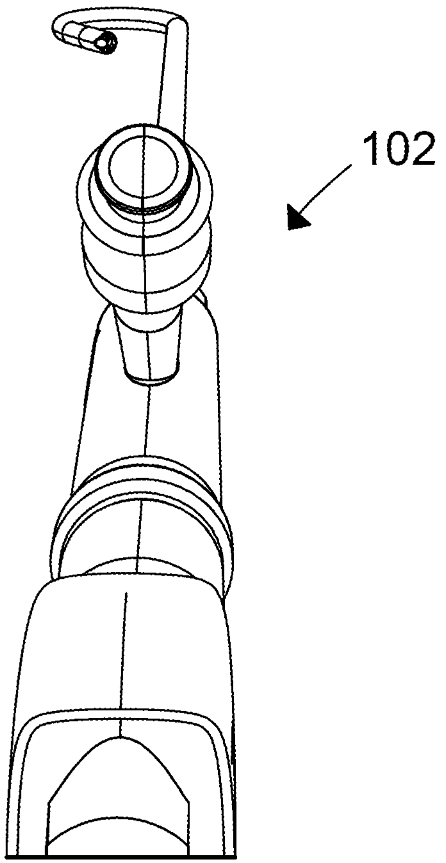
FIG. 18 illustrates yet another example of a view of forward facing cameras relating to determining PatPose from HandlePose, according to some embodiments.
Figure 19:
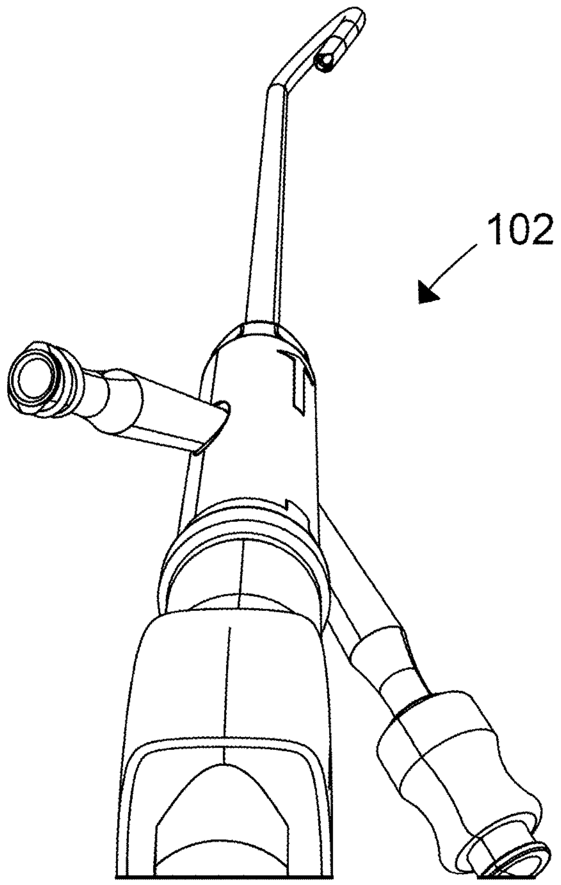
FIG. 19 illustrates yet another example of a view of forward facing cameras relating to determining PatPose from HandlePose, according to some embodiments.
Figure 20:
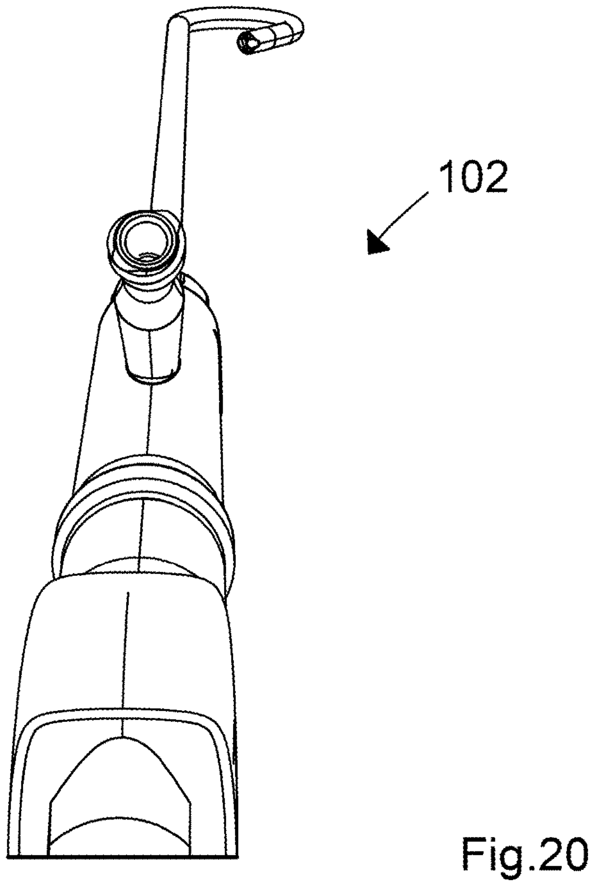
FIG. 20 illustrates another yet example of a view of forward facing cameras relating to determining PatPose from HandlePose, according to some embodiments.

FIG. 16 illustrates image processing segmentation involved in deriving CamPose from HandlePose as discussed above using images of single-use portion 102 taken with FFC 1002 or 1402 at reusable portion 104. At left in FIG. 16 is an image taken with FFC and at right is a segmented image that retains only the outlines or edges in the image on the left. This process can be carried out in processor 1008 (FIG. 10) or processor 302.

FIGS. 17-20 illustrate other examples of image processing segmentation involved in deriving CamPose from HandlePose showing single-use portion 102 in other orientations relative to reusable portion 104.

Figure 21:
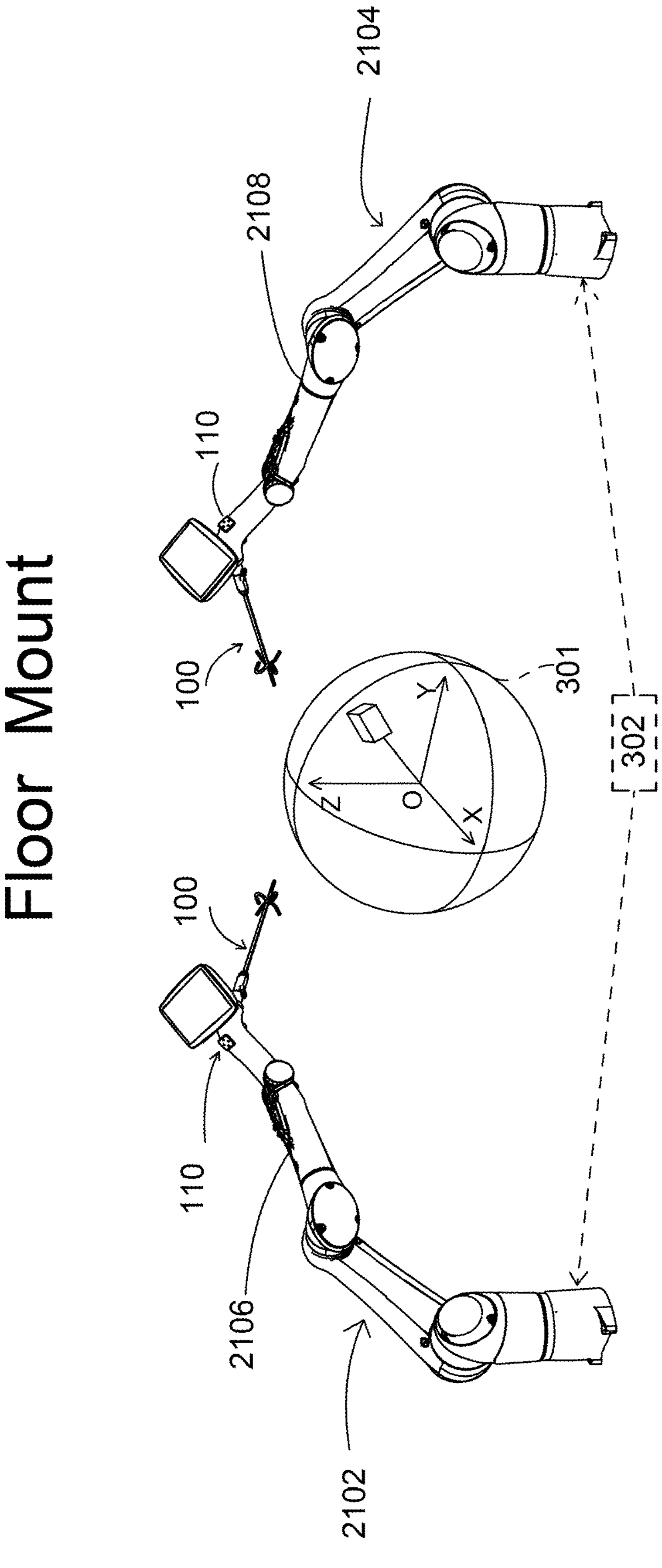
FIG. 21 is a perspective view of a floor-mounted compact robotic system and an object being examined or treated, according to some embodiments

FIG. 21 illustrates endoscopes 100 mounted to articulated robotic arms 2102 and 2104 that are table-mounted or floor mounted. Robotic arms 2102 and 2104 can be moved manually to position endoscopes 100 as desired in preparation for or during a medical procedure. A user can grasp a holder 2106 or 2108 in which handle 106 of endoscope 100 is received and manually operate controls 110 as discussed above. In addition, as desired or needed, unit 302 (FIG. 5) can command motion of robotic arms 2102 and 2104, and/or motion of step motors in endoscopes 100, as described above. As desired or needed, only a single robotic arm and endoscope can be used in a setting rather than the two shown in FIG. 21.

Figure 22:
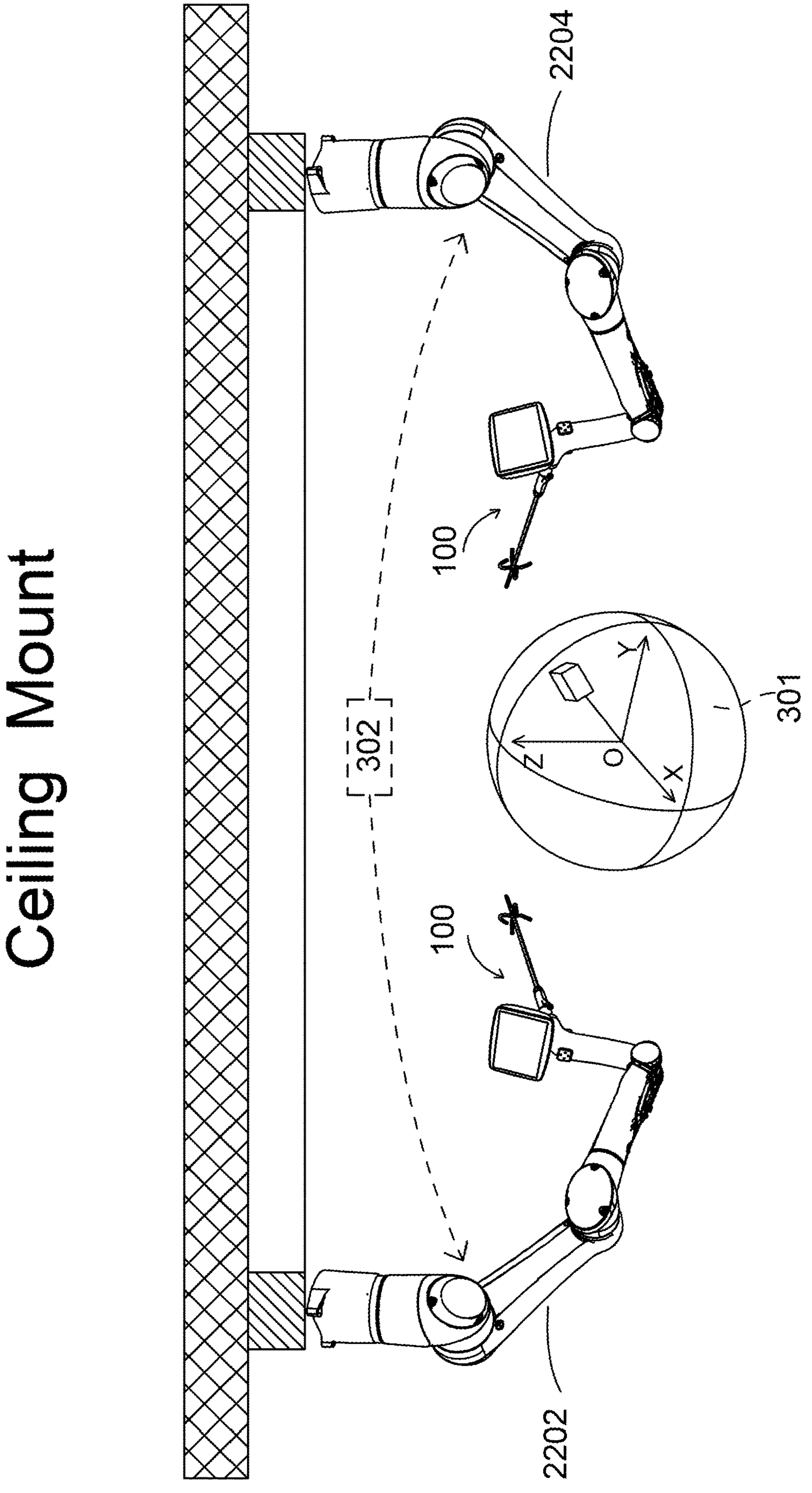
FIG. 22 is a perspective view of a ceiling-mounted compact robotic system and an object being examined or treated, according to some embodiments

FIG. 22 is otherwise like FIG. 21 but robotic arms 2202 and 2204 are mounted to a ceiling rather than to a table or floor. Alternatively, one or both robotic arms can be mounted to a wall.

Figure 23:
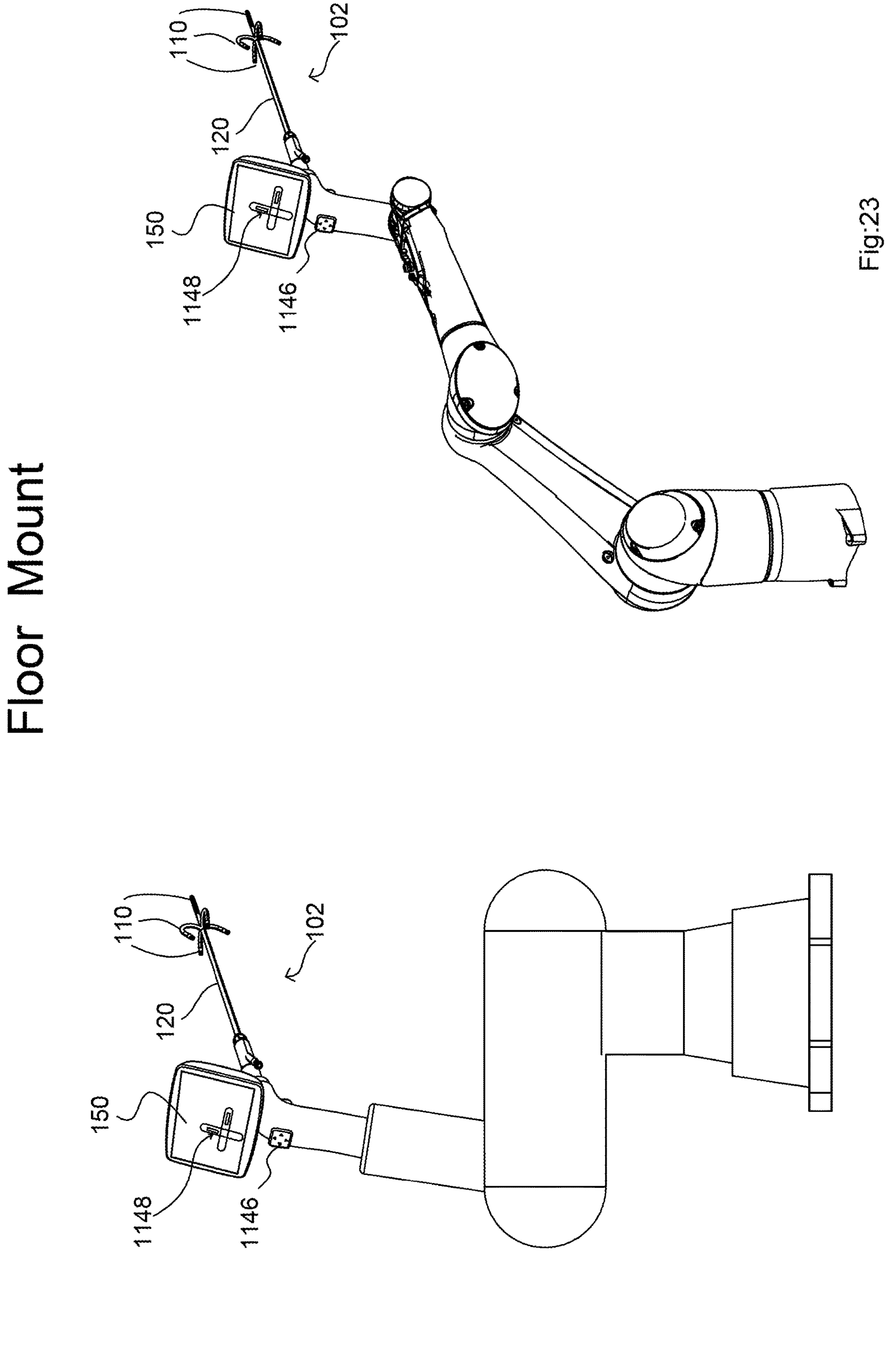
FIG. 23 is a perspective view of a floor-mounted or wall-mounted compact robotic system and an object being examined or treated, according to some embodiments

FIG. 23 is otherwise like FIG. 21 but endoscope 102 is mounted as illustrated and display 150 is touch sensitive showing crossing tracks 1148 along which a user can move a finger or a pointed to command the distal part 110 of cannula 120 to bend in a horizontal plane, a vertical plane, or a plane at an angle to the vertical and horizontal planes.

Figure 24:
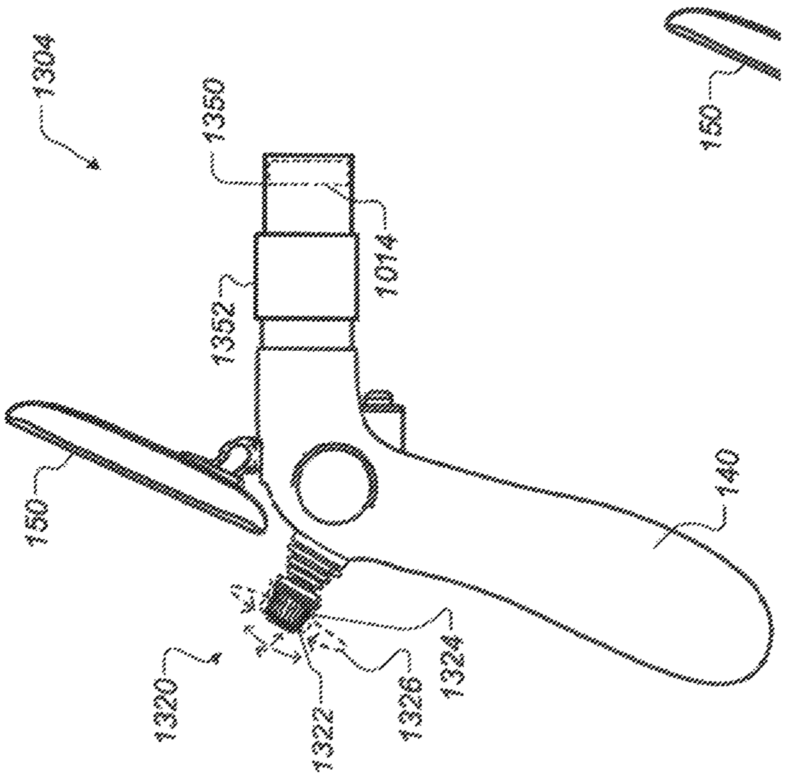
FIG. 24 is a schematic view of a compact robotic system operating in a scan mode to automatically acquire a scan of up to 360 degrees of the interior of an object.

FIG. 24 is a side view of a compact robotic endoscope that can be otherwise like those described or referenced above but has a control knob 1320 that can be conveniently operated by the thumb of a user holding handle 140. Knob 1320 is coupled to step motors 1006 (as in FIG. 13) to control bending if distal part 105 of cannula 107. The coupling can be configured such that a push on knob 1320 to the left or to the right on knob 1320 causes distal part 105 bend to the left or to the right through an angle determined by the force on the knob or the duration of the push, a push on the knob up or down causes the distal part 105 to bend up or down through an angle determined by the force or duration of the push, and a push onto the knob (in the distal direction) causes the angled distal part 105 to rotate through a predetermined angle around the long axis of cannula 107, such as 360 degrees, to thereby automatically image up to entire inside of a body cavity or organ. This imaging of up to the entire interior of a body cavity or organ is referred to as scan mode operation in this specification, and has been found to be particularly beneficial in certain medical procedures, for example by providing a convenient preview of all or at least a significant portion of the body cavity or organ before focusing on a suspicious area or lesion for examination or treatment.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

What it claimed is:

1. A compact, robotic-assisted endoscopic system comprising:

an endoscope comprising a single-use portion that includes a cannula with a camera at a distal end thereof and a reusable portion to which the single-use portion is releasably coupled to form the endoscope;

a first transducer arrangement mounted to at least one of the reusable and single-use portion and configured to derive measures of relative position of a selected part of the single-use portion relative to the reusable portion;

wherein the first transducer arrangement is configured to operate in one or more of the following modalities to track motion of the single-use portion relative to the reusable portion or another coordinate system:

laser tagging using time of flight;

ultrasound positioning using time of flight;

imaging at least one of the single-use and reusable portions with a VR headset with camera arrays;

RF tracking of a selected part of the single-use portion;

driving said cannula in selected motion with multiple degrees of freedom with step motors and tracking said motion by step motors operating parameters;

tracking motion of the single-use portion with a forward facing camera system (FFC) mounted to the reusable portion;

FFC tracking of reflective tags arranged on the single-use portion; and

FFC tracking of LEDs arranged on the single-use portion;

a processor receiving outputs of said first transducer arrangement related to said tracking motion of the single-use portion and configured to derive therefrom CamPose coordinates of a selected part of the single-use portion relative to the reusable portion or relative to another coordinate system; and a display configured to display images of an object being diagnosed or treated with said endoscope juxtaposed with images of said distal part of the single-use portion.

2. The endoscopic system of claim 1, further including a second transducer arrangement configured to measure HandlePose indicative of at least one of a position and orientation of the reusable portion relative to a selected coordinate system.

3. The endoscopic system of claim 2, in which at least a part of the second transducer arrangement is housed in said VR headset and is configured to measure HandlePose relative to the VR headset.

4. The endoscopic system of claim 2, in which at least a part of the second transducer arrangement is mounted at a selected position that does not change with movement of said endoscope and the second transducer arrangement and is configured to measure HandlePose relative to said selected position.

5. The endoscopic system of claim 1, including a source of guidance images related to a medical procedure on said object or like objects, including prior images of the object, standard images related to the object, and/or tutorial information related to the medical procedure.

6. A compact, robotic-assisted endoscopic system comprising:

an endoscope comprising a single-use portion that includes a cannula with a camera at a distal end thereof and a reusable portion to which the single-use portion is releasably coupled to form the endoscope;

a first transducer arrangement mounted to at least one of the reusable and single-use portion and configured to derive measures of relative position of a selected part of the single-use portion relative to the reusable portion;

wherein the first transducer arrangement is configured to operate in one or more of the following modalities to track motion of the single-use portion relative to the reusable portion or another coordinate system:

laser tagging using time of flight;

ultrasound positioning using time of flight;

imaging at least one of the single-use and reusable portions with a VR headset with camera arrays;

RF tracking of a selected part of the single-use portion;

driving the cannula in selected motion with multiple degrees of freedom with step motors and tracking the motion by step motors operating parameters;

tracking motion of the single-use portion with forward facing camera system (FFC) mounted to the reusable portion;

FFC tracking of reflective tags arranged on the single-use portion; and

FFC tracking of LEDs arranged on the single-use portion;

a second transducer arrangement configured to measure HandlePose indicative of at least one of a position and orientation of the reusable portion relative to a selected coordinate system;

a processor receiving outputs of the first transducer arrangement related to the tracking motion of the single-use portion and configured to derive therefrom CamPose coordinates of a selected part of the single-use portion relative to the reusable portion or relative to another coordinate system and receiving outputs from the second transducer; and a display configured to display images of an object being diagnosed or treated with the endoscope juxtaposed with images of the distal part of the single-use portion.

7. The endoscopic system of claim 6, in which at least a part of the second transducer is housed in the VR headset and is configured to measure HandlePose relative to the VR headset.

8. The endoscopic system of claim 6, in which at least a part of the second transducer arrangement is mounted at a selected position that does not change with movement of the endoscope and the second transducer arrangement and is configured to measure HandlePose relative to the selected position.

9. The endoscopic system of claim 6, including a source of guidance images related to a medical procedure on the object or like objects, including prior images of the object, standard images related to the object, and/or tutorial information related to the medical procedure.

* * * * *